(12) United States Patent
Bjoerkman et al.

(10) Patent No.: US 9,932,633 B2
(45) Date of Patent: Apr. 3, 2018

(54) METHODS FOR ASSESSING RNA QUALITY

(71) Applicant: Roche Molecular Systems, Inc., Pleasanton, CA (US)

(72) Inventors: Jens Bjoerkman, Oesersjoe (SE); Michael Kubista, Moelndal (SE)

(73) Assignee: Roche Molecular Systems, Inc., Pleasanton, CA (US)

( * ) Notice: Subject to any disclaimer, the term of this patent is extended or adjusted under 35 U.S.C. 154(b) by 19 days.

(21) Appl. No.: 14/385,602

(22) PCT Filed: Mar. 20, 2013

(86) PCT No.: PCT/EP2013/055832
§ 371 (c)(1),
(2) Date: Sep. 16, 2014

(87) PCT Pub. No.: WO2013/139860
PCT Pub. Date: Sep. 26, 2013

(65) Prior Publication Data
US 2015/0044685 A1    Feb. 12, 2015

(30) Foreign Application Priority Data
Mar. 21, 2012 (EP) .................................. 12160602

(51) Int. Cl.
*C12Q 1/68* (2018.01)

(52) U.S. Cl.
CPC ........... *C12Q 1/686* (2013.01); *C12Q 1/6809* (2013.01)

(58) Field of Classification Search
CPC .............................. C12Q 1/6809; C12Q 1/686
See application file for complete search history.

(56) References Cited

U.S. PATENT DOCUMENTS

| | | | |
|---|---|---|---|
| 5,118,801 | A | 6/1992 | Lizardi et al. |
| 5,210,015 | A | 5/1993 | Gelfand et al. |
| 5,487,972 | A | 1/1996 | Gelfand et al. |
| 5,538,848 | A | 7/1996 | Livak et al. |
| 5,804,375 | A | 9/1998 | Gelfand et al. |
| 6,174,670 | B1 | 1/2001 | Wittwer et al. |

FOREIGN PATENT DOCUMENTS

| | | | |
|---|---|---|---|
| WO | 199746712 | A2 | 12/1997 |
| WO | 199746714 | A1 | 12/1997 |
| WO | 19979746707 | A2 | 12/1997 |
| WO | 2005090609 | A1 | 9/2005 |
| WO | PCTEP2013055832 | | 3/2013 |
| WO | PCTEP2013055832 | | 7/2013 |

OTHER PUBLICATIONS

Duborjal, H. et al., Genome Res., vol. 12, pp. 1901-1909 (2002).*
Galivetti, C.R. et al., RNA, vol. 16, pp. 450-461 (2010).*
Nelson, D.L. et al., PNAS USA, vol. 86, pp. 6686-6690 (1989).*
Antonov, J. et al. (Lab. Invest., vol. 85, pp. 1040-1050 (2005).*
High-Capacity cDNA Archive Kit from Applied Biosystems, pp. 1-32 (2000).*
Andersen, Claus Lindbjerg, et al., 2004, "Normalization of Real-Time Quantitative Reverse Transcription-PCR Data: A Model-Based Variance Estimation Approach to Identity Genes Suited for Normalization, Applied to Bladder and Colon Cancer Data Sets", Cancer Research, 64:5245-5250.
Bernard, Philip S., et al.,1998, "Integrated Amplification and Detection of the C677T Point Mutation in the Methylenetetrahydrofolate Reductase Gene by Fluorescence Resonance Energy Transfer and Probe Melting Curves", Analytical Biochemistry, 255:101-107.
Brunner, Amy M., et al., 2004, "Validating internal controls for quantitative plant gene expression studies", BMC Plant Biology, 4(14):1-7.
Matthews, Jayne A., et al.,1988, "Analytical Strategies for the Use of DNA Probes", Analytical Biochemistry, 169:1-25.
Nolan, Tania, et al., 2006, "Quantification of mRNA using real-time RT-PCR", Nature Protocols, 1(3):1559.
Pfaffl, Michael W., et al., 2004, "Determination of stable housekeeping genes, differentially regulated target genes and sample integrity: BestKeeper—Excel-based tool using pair-wise correlations", Biotechnology Letters, 26:509-515.
Schroeder, Andreas, et al., 2006, "The RIN: an RNA integrity number for assigning integrity values to RNA measurements", Methodology article, 7/3:1-14.
Sharova, Lioudmila V., et al., 2008, "Database for mRNA Half-Line of 19 977 Genes Obtained by DNA Microarray Analysis of Pluripotent and Differentiating Mouse Embryonic Stem Cells", DNA Research, 16:45-58.
Sugita, Michio, et al., 2001, "One-Step Duplex Reverse Transcription-Polymerase Chain Reaction for Quantitative Assessment of RNA Degradation", Analytical Biochemistry, 295:113-116.
Swift, Galvin H., et al., 2000, "Assessment of RNA Quality by Semi-Quantitiative RT-PCR of Multiple Regions of a Long Ubiquitous mRNA", BioTechniques, 28(3):524-531.
Vandesompele, Jo, et al., 2002, "Accurate normalization of real-time quantitative RT-PCR data by geometric averaging of multiple internal control genes", Genome Biology, 3(7).
Yang, G., et al., 2008, "Simple and Efficient Isolation of High-Quality Total RNA from Hibiscus tiliaceus, a Mangrove Associate and Its Relatives", Preparative Biochemistry and Biotechnology, 38(3):257-264.

* cited by examiner

*Primary Examiner* — Teresa E Strzelecka
(74) *Attorney, Agent, or Firm* — Carol Johns; Olga Kay

(57) ABSTRACT

The present description refers to methods and kits for the assessment of RNA quality in a sample. Stable RNA is used as a reference for the assessment of RNA quality, wherein the stable RNA has low susceptibility to nuclease degradation.

14 Claims, 19 Drawing Sheets

```
                         SEQUENCE LISTING

<160> NUMBER OF SEQ ID NOS: 50

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
atgaaacccc cagccataac                                              20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ggtgcccaaa gaatcagaac                                              20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
tgtagagcac ccgaaaccac                                              20

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
ccaaaggagg gaagaacga                                               19

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
ggaattgtac cgcagctt                                                18
```

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
acgaagtgca atggtcttta        20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ttcccagcct taaaaggtct        20

<210> SEQ ID NO 8
<211> LENGTH: 16
<212> TYPE: DNA
<213> ORGANISM: Artificial Sequence
<220> FEATURE:
<223> OTHER INFORMATION: primer

<400> SEQUENCE: 8
ggctgctcac aggcta        16

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tgtttgtgat gggtgtgaac        20

<210> SEQ ID NO 10
<211> LENGTH: 16
<212> TYPE: DNA
<213> ORGANISM: Artificial Sequence
<220> FEATURE:
<223> OTHER INFORMATION: primer

<400> SEQUENCE: 10
tgggtggcag tgatgg        16

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tcctaaagca tacaggtcct        20

<210> SEQ ID NO 12
<211> LENGTH: 17
<212> TYPE: DNA
<213> ORGANISM: Artificial Sequence
<220> FEATURE:

```
<223> OTHER INFORMATION: primer

<400> SEQUENCE: 12
agaccacatg cttgcca                                                    17

<210> SEQ ID NO 13
<211> LENGTH: 16
<212> TYPE: DNA
<213> ORGANISM: Artificial Sequence
<220> FEATURE:
<223> OTHER INFORMATION: primer

<400> SEQUENCE: 13
gtgtgcctac cctgcg                                                     16

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
acttactggg aattcctcgt                                                 20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
gagactctgg catgctaact                                                 20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
ggacttaatc aacgcaagct                                                 20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
gttgaacccc attcgtgatg                                                 20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
ggacttaatc aacgcaagct                                                 20
```

```
<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
ggggattgca attattcccc                                              20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
ggacttaatc aacgcaagct                                              20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
gtttactcac gtcatccagc                                              20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
gcaagcaagc agaatttgga                                              20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
aaaagatgag tatgcctgcc                                              20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
gcaagcaagc agaatttgga                                              20

<210> SEQ ID NO 25
<211> LENGTH: 20
<212> TYPE: DNA
<213> ORGANISM: Artificial Sequence
<220> FEATURE:
<223> OTHER INFORMATION: primer
```

-continued

<400> SEQUENCE: 25
gatcgagaca tgtaagcagc                                              20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
gcaagcaagc agaatttgga                                              20

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
cccgatatgg cgtttccccg c                                            21

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
cggatcagac gaagaggggc gt                                           22

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
cccgatatgg cgtttccccg c                                            21

<210> SEQ ID NO 30
<211> LENGTH: 25
<212> TYPE: DNA
<213> ORGANISM: Artificial Sequence
<220> FEATURE:
<223> OTHER INFORMATION: primer

<400> SEQUENCE: 30
aagatggtta ggtctacgga ggctc                                        25

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
cccgatatgg cgtttccccg c                                            21

<210> SEQ ID NO 32
<211> LENGTH: 22

```
<212> TYPE: DNA
<213> ORGANISM: Artificial Sequence
<220> FEATURE:
<223> OTHER INFORMATION: primer

<400> SEQUENCE: 32
gcagatgcga gcaggagtag ga                                         22

<210> SEQ ID NO 33
<211> LENGTH: 25
<212> TYPE: DNA
<213> ORGANISM: Artificial Sequence
<220> FEATURE:
<223> OTHER INFORMATION: primer

<400> SEQUENCE: 33
cagttggtgg tctaaccgga attgt                                      25

<210> SEQ ID NO 34
<211> LENGTH: 22
<212> TYPE: DNA
<213> ORGANISM: Artificial Sequence
<220> FEATURE:
<223> OTHER INFORMATION: primer

<400> SEQUENCE: 34
cgtgaagcac gatgtcaagg ga                                         22

<210> SEQ ID NO 35
<211> LENGTH: 25
<212> TYPE: DNA
<213> ORGANISM: Artificial Sequence
<220> FEATURE:
<223> OTHER INFORMATION: primer

<400> SEQUENCE: 35
cagttggtgg tctaaccgga attgt                                      25

<210> SEQ ID NO 36
<211> LENGTH: 24
<212> TYPE: DNA
<213> ORGANISM: Artificial Sequence
<220> FEATURE:
<223> OTHER INFORMATION: primer

<400> SEQUENCE: 36
tgtgtcatct agggtgaagc ctga                                       24

<210> SEQ ID NO 37
<211> LENGTH: 25
<212> TYPE: DNA
<213> ORGANISM: Artificial Sequence
<220> FEATURE:
<223> OTHER INFORMATION: primer

<400> SEQUENCE: 37
cagttggtgg tctaaccgga attgt                                      25

<210> SEQ ID NO 38
<211> LENGTH: 25
<212> TYPE: DNA
<213> ORGANISM: Artificial Sequence
<220> FEATURE:
<223> OTHER INFORMATION: primer

<400> SEQUENCE: 38
```

```
tgtggtgtaa gcatctgggt agtct                                         25

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
ctagagctaa tacatgccga                                               20

<210> SEQ ID NO 40
<211> LENGTH: 19
<212> TYPE: DNA
<213> ORGANISM: Artificial Sequence
<220> FEATURE:
<223> OTHER INFORMATION: Primer

<400> SEQUENCE: 40
gatgtggtag ccgtttctc                                                19

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
cgtctgccct atcaactttc                                               20

<210> SEQ ID NO 42
<211> LENGTH: 19
<212> TYPE: DNA
<213> ORGANISM: Artificial Sequence
<220> FEATURE:
<223> OTHER INFORMATION: Primer

<400> SEQUENCE: 42
gatgtggtag ccgtttctc                                                19

<210> SEQ ID NO 43
<211> LENGTH: 23
<212> TYPE: DNA
<213> ORGANISM: Artificial Sequence
<220> FEATURE:
<223> OTHER INFORMATION: Primer

<400> SEQUENCE: 43
tgctgtgata aaccaaagat gag                                           23

<210> SEQ ID NO 44
<211> LENGTH: 18
<212> TYPE: DNA
<213> ORGANISM: Artificial Sequence
<220> FEATURE:
<223> OTHER INFORMATION: Primer

<400> SEQUENCE: 44
gtcacctggg accgagac                                                 18

<210> SEQ ID NO 45
<211> LENGTH: 21
<212> TYPE: DNA
<213> ORGANISM: Artificial Sequence
```

```
<220> FEATURE:
<223> OTHER INFORMATION: Primer

<400> SEQUENCE: 45
atggtgtgct cattgctatt c                                              21

<210> SEQ ID NO 46
<211> LENGTH: 18
<212> TYPE: DNA
<213> ORGANISM: Artificial Sequence
<220> FEATURE:
<223> OTHER INFORMATION: Primer

<400> SEQUENCE: 46
gtcacctggg accgagac                                                  18

<210> SEQ ID NO 47
<211> LENGTH: 19
<212> TYPE: DNA
<213> ORGANISM: Artificial Sequence
<220> FEATURE:
<223> OTHER INFORMATION: Primer

<400> SEQUENCE: 47
tagacacccg agcctactt                                                 19

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
gctcatgtgt catttagggt                                                20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
agctcacttc cactatgtct                                                20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
gctcatgtgt catttagggt                                                20
```

METHODS FOR ASSESSING RNA QUALITY

BACKGROUND OF THE INVENTION

Figure 1A:
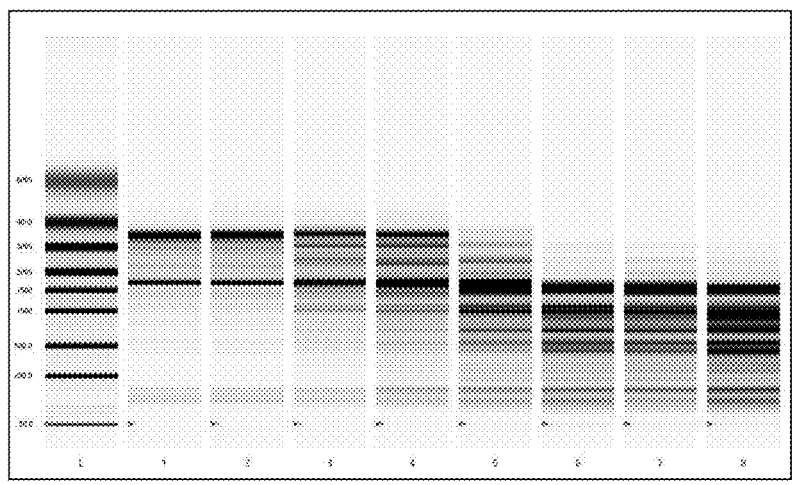

The present description refers to methods and kits for the assessment of RNA quality in a sample. Stable RNA is used as a reference for the assessment of RNA quality, wherein the stable RNA has low susceptibility to nuclease degradation.

Nucleic acid analysis is most important in molecular diagnostics and molecular research. For quantitative analysis the most popular and accurate technology is quantitative real-time polymerase chain reaction (qPCR). Specific DNA targets are easy to quantify with qPCR. The DNA molecule is stable, resistant, and easy to purify. RNA targets are much more challenging. The RNA molecule is not particularly stable. It is self-cleaved at low as well as high pH and at elevated temperature. It is susceptible to UV-light and many chemicals, which either cleave it or modify it such that the RNA cannot be reverse transcribed into cDNA for subsequent qPCR analysis, it is also prone to cleavage by nucleases. Degraded RNA may escape detection and partially degraded RNA may be erroneously quantified. Even in relative quantification, when the indicator is the relative amount of two RNAs, RNA integrity is essential, since degradation may affect the compared RNAs differently. The importance of RNA quality in quantitative analysis has led to the development of methods to assess sample integrity. By far most common method is electrophoresis. The RNA contained in a matrix is separated based on length in an electric field and stained. Initially agarose gels were used, but have been replaced by more powerful systems such as capillary electrophoresis and microfluidics represented by the Bioanalyzer (Agilent), Experion™ System (Bio-Rad), QIAxel (Qiagen) and the ScreenTape (Agilent). These systems analyze the electrophoretic traces based on which the integrity is quantified as the RNA Integrity Number (RIN), RNA quality indicator (RQI), RNA Integrity Number Equivalent (RINe) and equivalent. The approach works well, but suffers from the fact that most of the RNA, typically >80%, is ribosomal RNA (rRNA) and the electropherogram is dominated by the 18S and 28S rRNA species (in mammalian systems). Hence, the approach assesses the quality of rRNA rather than of the targeted mRNA. Since rRNA molecules are very different from mRNA molecules, for example they have neither 5'-CAP nor A-tail and they are complexed with ribosomal proteins in the cell, they may experience different degradation. Hence, the quality measure obtained from electrophoretic analysis of RNA may not be relevant for expression analysis.

A method to assess the integrity of mRNA directly is known in the art (WO 2005/090609 A1; Swift et al., BioTechniques 28 (2000) 524-531). The method is based on directed reverse transcription of the RNA molecule to produce cDNA. The reverse transcription is initiated at the mRNA 3'-end by hybridizing an oligo(T) primer to the A-tail of mRNA or by hybridizing a gene specific primer to a particular mRNA target. The cDNA is then amplified using two PCR assays targeting sequences at different distances from the RT primer. One PCR assay amplifies a sequence closer to the RT primer and hence to the mRNA 3'-end and the other PCR assay amplifies a sequence further away from the RT primer. The two PCR assays may share reverse primer, if they extend differently, but not the forward primer. If the mRNA was intact the RT primer is expected to be extended all the way to the mRNA 5'-end and the two PCR assays shall produce the same amount of amplicon, which is readily measured if the PCR is performed as qPCR. However, if the mRNA was partially degraded the RT primer could not be extended beyond the break-point and the assay further away from the priming site (closer to the mRNA 5'.end) would yield less amplicon than the assay nearer to the RT primer (closer to the mRNA 3'-end). In the literature this approach to assess RNA quality has become known as the 3'/5' assay (Nolan et al., Nat. Protoc. 1 (2006) 1559-1582). The 3'/5' assay performs well on rather pure material that is not too degraded. Most field samples are of poorer quality. If a sample contains fragmented nucleic acids or oligonucleotides (even very short ones), these will act as primers in the reverse transcription, and the effect of the necessary directional priming will be obscured. Since all degraded samples contain fragments that may prime the reverse transcription the dynamic range of the 3'/5' assay is inherently limited. Another limitation of the 3'/5' assay is that it only detects partially fragmented RNA; it will not reflect total loss of mRNA due to degradation. This is serious drawback since nucleolytic degradation, which is of major concern in biological samples, often degrades an mRNA fully once degradation is initiated. Exonucleases bind either the 3' or 5' end of the mRNA and degrades its full length to very short fragments. These fragments go undetected by the 3'/5' assay.

In this context, the technical problem underlying the present description was to provide an improved method which overcomes the above drawbacks and allows for a more accurate assessment of the quality of the RNA used as a starting material for analysis and in particular for RT-qPCR experiments.

SUMMARY OF THE INVENTION

The present description is directed to a method for the quality control of RNA used as a starting material for RNA analysis in particular by RT-qPCR. The improvement is based on the fact that the assay for assessing the quality is performed using RNA which is highly resistant to degradation processes, particularly to degradation processes caused by nucleases. More precisely, the present description is directed to a method for RNA quality control in real-time PCR experiments, the method comprising the steps of preparing cDNA from RNA, quantifying by amplification at least one amplicon of a first cDNA, wherein the first cDNA derives from mRNA, quantifying by amplification at least one amplicon of a second cDNA, wherein the second cDNA derives from comparably stable "tester" RNA such as ribosomal RNA, mitochondrial RNA, chloroplast RNA and small nuclear RNA, assessing the quality of the mRNA by comparing the amount of the at least one amplicon of the first cDNA with the amount of the at least one amplicon of the second cDNA. In most cases the stable RNA has low susceptibility to nuclease degradation.

In one embodiment optionally the following steps are performed separately from the two quantification steps and the assessment step described in the previous paragraph. Quantifying by amplification at least two amplicons of the second cDNA, and assessing the quality of the stable RNA by comparing the amounts of the at least two amplicons of the second cDNA.

In one embodiment, the above step of preparing cDNA from RNA is performed by using random sequence primers, oligo-dT-primers, sequence specific primers or a mixture thereof. In one embodiment, the mRNA derives from a gene with an expression that is essentially invariant of the physiological status of a cell, in a particular when a drug treatment is being studied. In one embodiment, the mRNA derives from Alu repeats.

In one embodiment the testing RNA is a mitochondrial RNA or chloroplast RNA. In a specific embodiment the mitochondrial RNA is MTCO1.

In another embodiment, the testing RNA is a ribosomal RNA. In still another embodiment the testing RNA is a small nuclear RNA such as U3, U6 or the like. In a specific embodiment, said testing RNA is selected from a group of U3 and 18s RNA.

In one embodiment the comparison of the step of assessing the quality of the mRNA in the sample is performed using the geometric mean expression of multiple mRNAs. In one embodiment the amplification of the at least two amplicons of the second cDNA is performed using one common primer for the at least two amplicons. In one embodiment, at least one of the primers used for preparing cDNA from RNA present in the sample is identical to at least one of the primers used for the quantification by amplification of at least one amplicon of the second cDNA, wherein the second cDNA derives from stable RNA. In one embodiment, the first of the at least two amplicons mentioned above has a length of less than 100 bp and the second of the at least two amplicons mentioned above has a length of at least 100 bp.

The present description is further directed to a kit for assessing RNA quality, the kit comprising a first set of primers for preparing cDNA from RNA, a second set of primers for the amplification of at least one amplicon of a first cDNA, wherein the first cDNA derives from mRNA, a third set of primers for the amplification of at least one amplicon of a second cDNA, wherein the second cDNA derives from stable RNA, wherein the stable RNA has low susceptibility to nuclease degradation.

In one embodiment, the first set of primers comprises random sequence primers, oligo-dT-primers, sequence specific primers or a mixture thereof. In one embodiment, the second set of primers specifically binds within a gene with an expression that is essentially invariant of the treatment studied. In a specific embodiment, the second set of primers specifically binds within Alu repeats. In one embodiment, the third set of primers is designed such that at least two amplicons are amplified, the first of the at least two amplicons has a length of less than 100 bp and wherein the second of the at least two amplicons has a length of at least 100 bp. In one embodiment, the amplification of the at least two amplicons is performed using one common primer. In one embodiment, at least one of the primers of the first set of primers is identical to at least one of the primers of the third set of primers. In one embodiment, the stable RNA is a mitochondrial RNA or chloroplast RNA. In a specific embodiment, the mitochondrial RNA is MTCO1.

FIGURES

FIG. 1: Electropherogram traces showing separation of RNA fragments extracted at different time points from liver. FIG. 1A shows in left lane molecular size markers followed by lanes 1-8 showing RNA extracted from grounded liver aged 0, 1, 5, 10, 30, 60, 90 and 120 minutes. FIG. 1B shows in left lane molecular size markers followed by lanes 1-6 showing RNA extracted from liver tissue in pieces aged 0, 10, 20, 40, 60 and 120 minutes. The two intense bands appearing most clearly in lane 1 in both graphs reflect intact 18S and 28S rRNA. As the RNA degrades with time faster migrating bands appear reflecting short fragments. FIGS. 1C and 1D show the decrease of the RNA Quality Index (RQI) with time of aging during 120 minutes in the sample in form of powder and pieces, respectively. FIGS. 1E and 1F show the degradation of individual RNAs in the samples (powder and pieces) measured with RT-qPCR. Increased Cq values reflect reduction in the amount of amplifiable material caused by degradation.

Figure 2A:
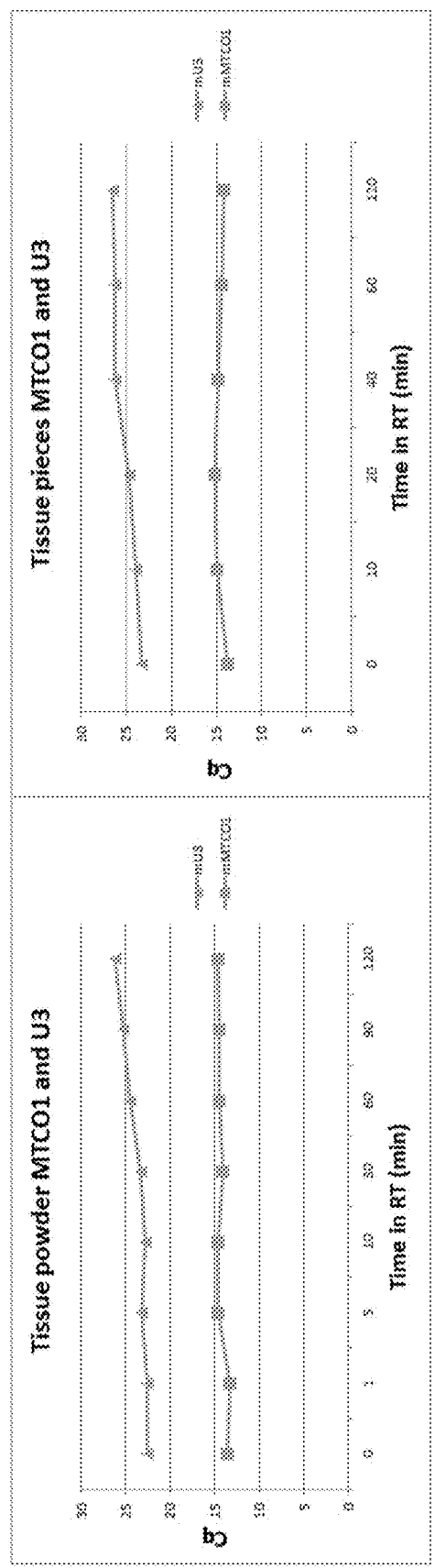
Figure 2B:
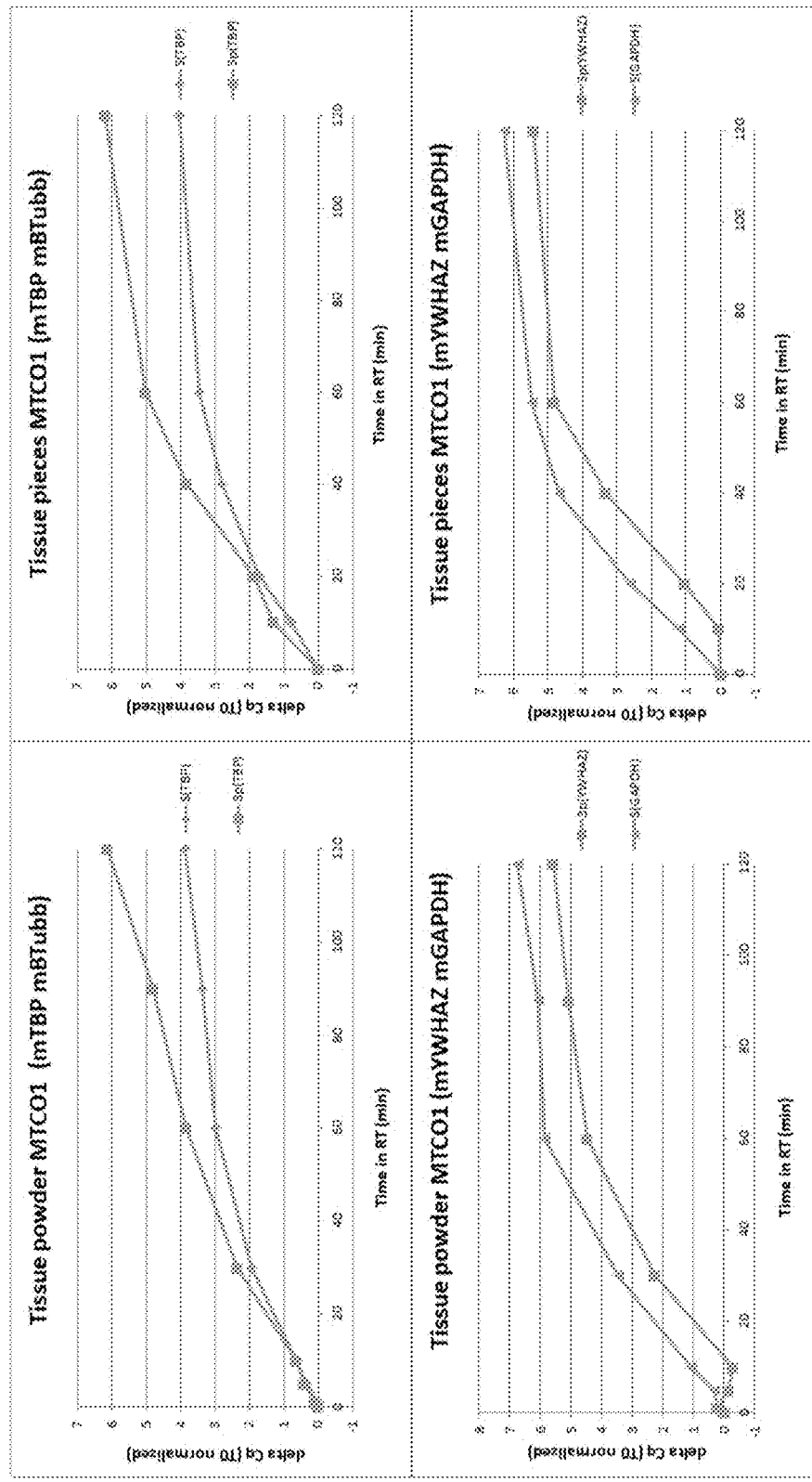
Figure 2C:
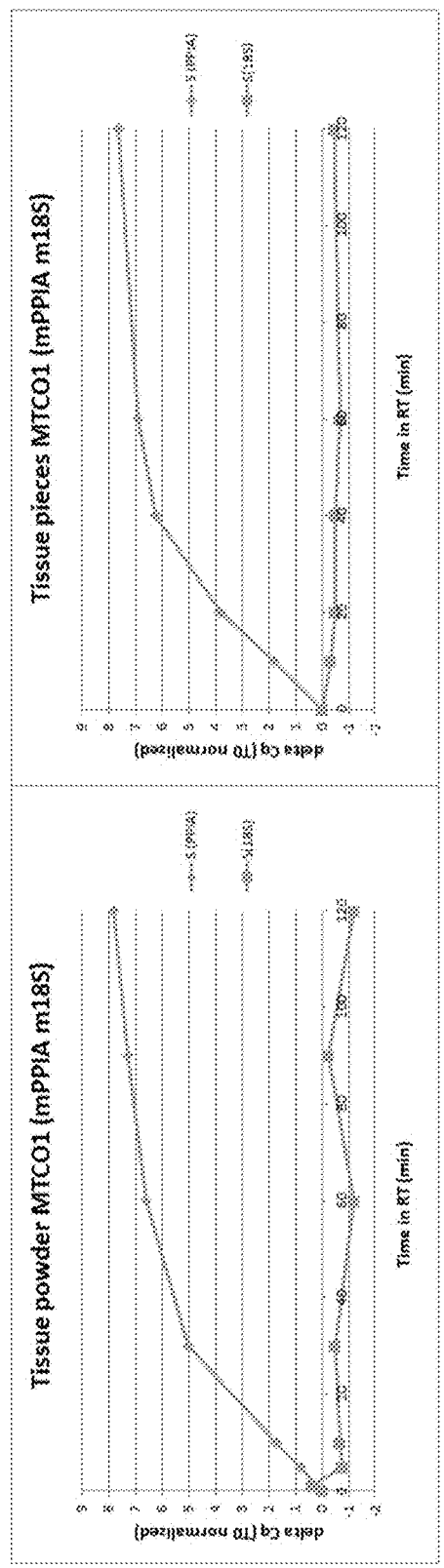

FIG. 2: The amounts of MTCO1 and U3 of aged liver as a function of time after thawing measured with RT-qPCR. The left panel of FIG. 2A shows the result for liver grounded into powder. The right panel of FIG. 2A shows the result for liver cut into pieces. FIG. 2B shows the comparison of MTCO1 with common reference genes: TBP, YWHAZ, and GAPDH used for normalization of RNA levels in quantitative analysis. The data are presented as differences in Cq values normalized to 0 at time 0 before the onset of degradation. FIG. 2C compares MTCO1 with the common reference gene PPIA and with the structural 18S RNA (left graph: liver powder; right graph: liver pieces). Extensive degradation of PPIA and stability of 18S RNA upon aging is clearly reflected.

Figure 3:
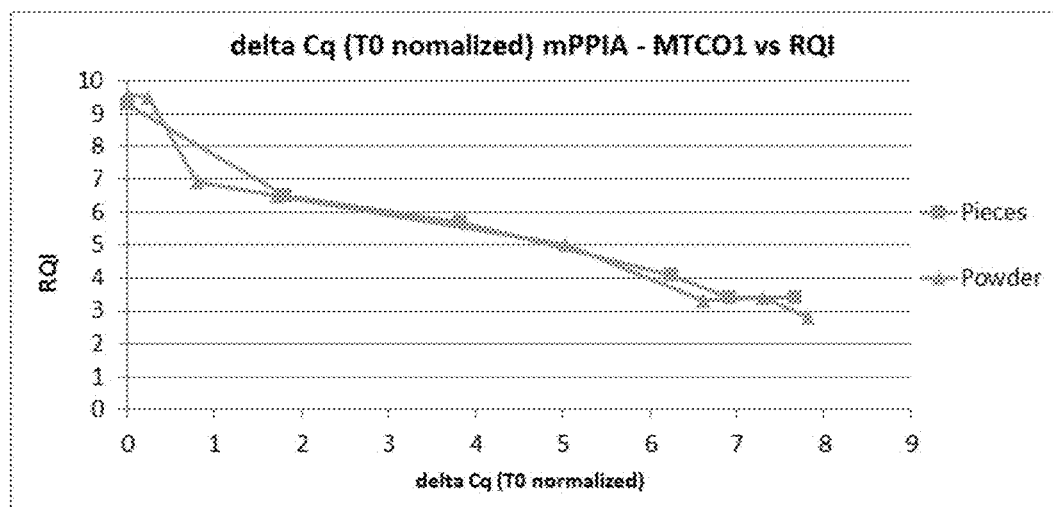

FIG. 3: RNA integrity assessed based on markers MTCO1 and PPIA is compared to RNA integrity assessed by capillary electrophoresis.

Figure 4:
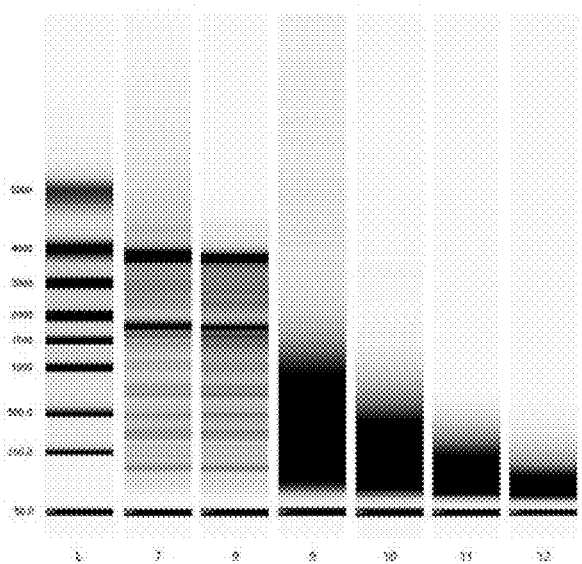

FIG. 4: RNA degradation induced by heat and analyzed with capillary electrophoresis in the Experion. Lane L is molecular size markers. Lanes 7-11 show RNA degraded by heat for 0, 1, 10, 20, 40 and 60 min.

FIG. 5: The letters S, M and L as used herein refer to the lengths of the amplicons produced in the respective assays (S: short amplicon, <100 bp; M: medium amplicon, 100-200 bp; L: long amplicon, >300 bp). Shown in FIG. 5A is the amount of PCR product produced by the M assay relative to the L assay (M:L); the S assay relative to the L assay (S:L), and the S assay relative to the M assay (S:M). FIG. 5B compares the sensitivities of measurement of RNA quality with capillary electrophoresis quantified as RQI with measurements of expression ratios according to the present description using 18S rRNA as reporter upon heat induced RNA degradation. FIG. 5C shows the L:M, L:S and M:S ratios using B2M as reporter measured as function of time of heat induced RNA degradation. All three ratios increase with incubation time. The L:M and L:S ratios can only be followed for the first 20 minutes of degradation. FIG. 5D compares the sensitivities of measurement of RNA quality with capillary electrophoresis quantified as RQI with measurements of expression ratios according to the present description using B2M as reporter upon heat induced RNA degradation. FIG. 5E shows the L:M, L:S and M:S ratios using MTCO1 as reporter measured as function of time of heat induced RNA degradation. All three ratios increase with incubation time and can be followed throughout the entire course of 60 minutes of degradation.

FIG. 6: Measured electropherograms as function of UV irradiation are shown in FIG. 6A. Lane L is molecular size markers and lanes 1-6 show RNA degraded by UV irradiation for 0, 1, 10, 20, 40 and 60 min. FIG. 6B shows changes in the L:M, L:S and M:S amplicon ratios using marker 18S RNA. FIG. 6C compares RNA quality assessed by measuring the L:M and L:S ratios using marker 18S RNA with RNA quality assessed using capillary electrophoresis and quantified as RQI. FIG. 6D shows changes in the L:M, L:S and M:S amplicon ratios using marker B2M. FIG. 6E shows the comparison of the measured relative amplicon yields based on the present description using B2M and RQI numbers determined using current state of the art capillary electrophoresis. FIG. 6F shows the results obtained using the present description with marker MTCO1.

Figure 7:
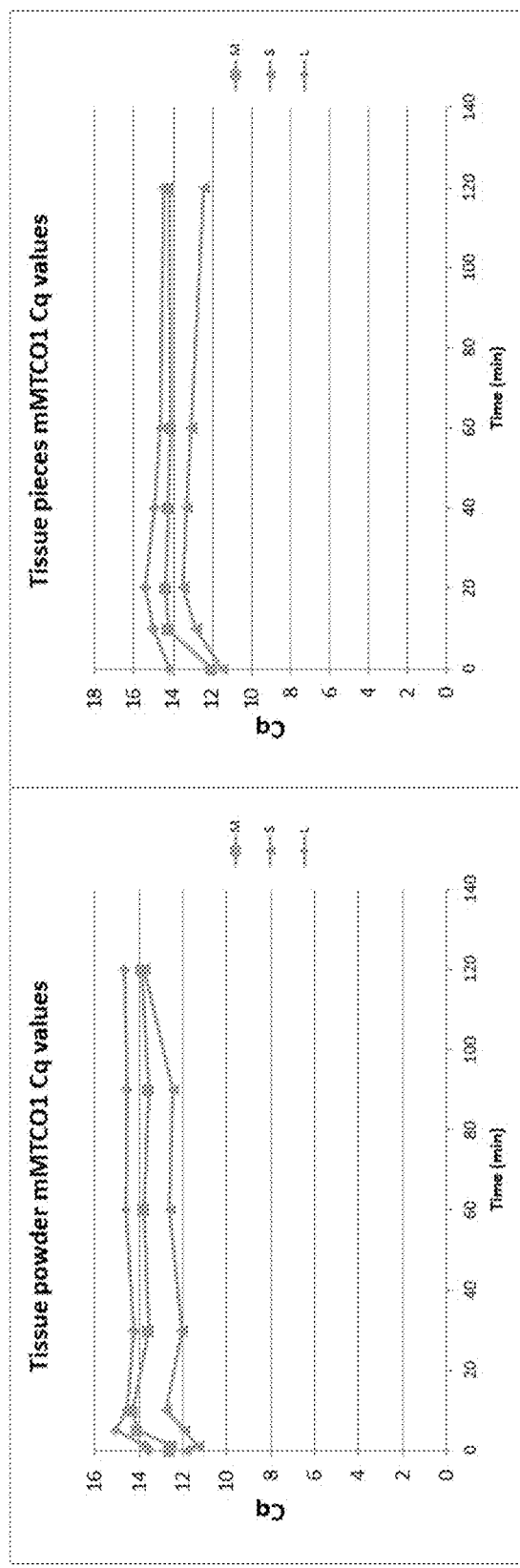

FIG. 7: Comparison of the yields of the three different length amplicons of MTCO1 on the liver samples degraded by aging. Powder is represented in the left panel and pieces in the right panel. No variation in the relative yields of the three amplicons with time is observed under these conditions of degradation.

FIG. 8: FIG. 8A shows analysis results with the present description based on three different lengths amplicons of marker MTCO1 of five formalin fixed paraffin embedded (FFPE) breast tissue samples. FIG. 8B shows the same data as in FIG. 8A, but presented as differences between the measured Cq's ($\Delta$Cq) of the amplicons. FIG. 8C shows the result of the analysis of FFPE arteria samples, which were analyzed using three different lengths amplicons of marker 18S. FIG. 8D presents the data in FIG. 8C as $\Delta$Cq's, reflecting the relative abundance of the differentially long 18S amplicons.

Figure 9:
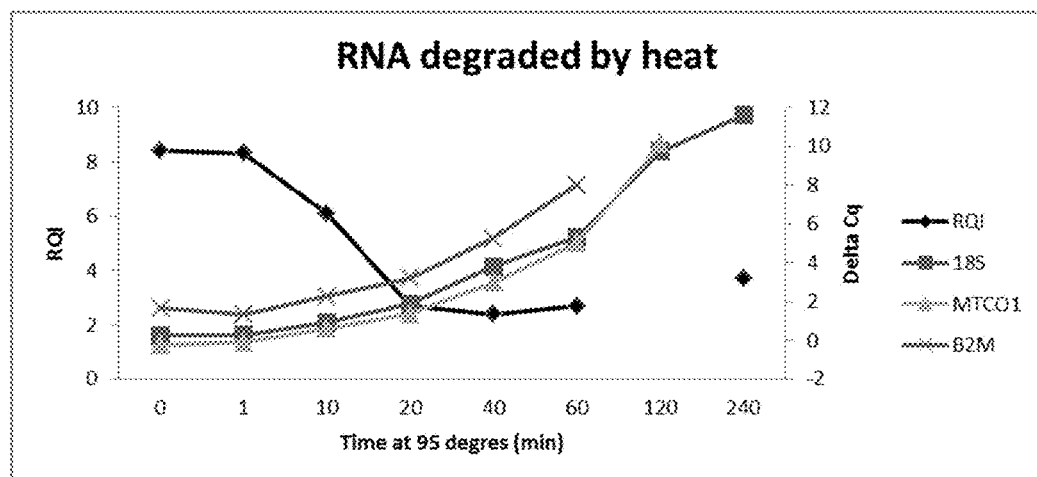

FIG. 9: The Figure shows monitoring of rat RNA degradation at 95° C. Depicted is the comparison of RQI measured with the capillary electrophoresis system (Experion, Bio-Rad) with L:S (long and short qPCR assays). RQI drops dramatically during first 20 minutes and then levels off revealing no more degradation, while L:S reflects degradation throughout 2 h. The RQI after 240 minutes is higher than after 20 minutes. The x-axis scale is not linear.

Figure 10:
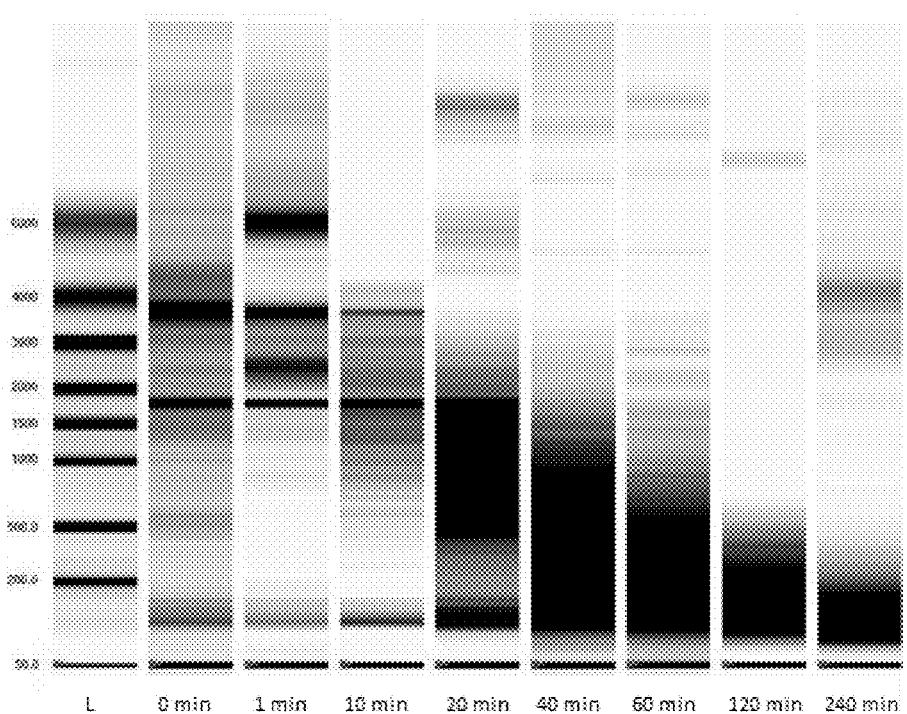

FIG. 10: The Figure shows a gel image derived from Experion™ System (Bio-Rad) of rat RNA degraded at 95° C. The left lane is a molecular size ladder. Intact 28 S RNA appears at 3800 bp and intact 18S RNA at 1800 bp.

Figure 11:
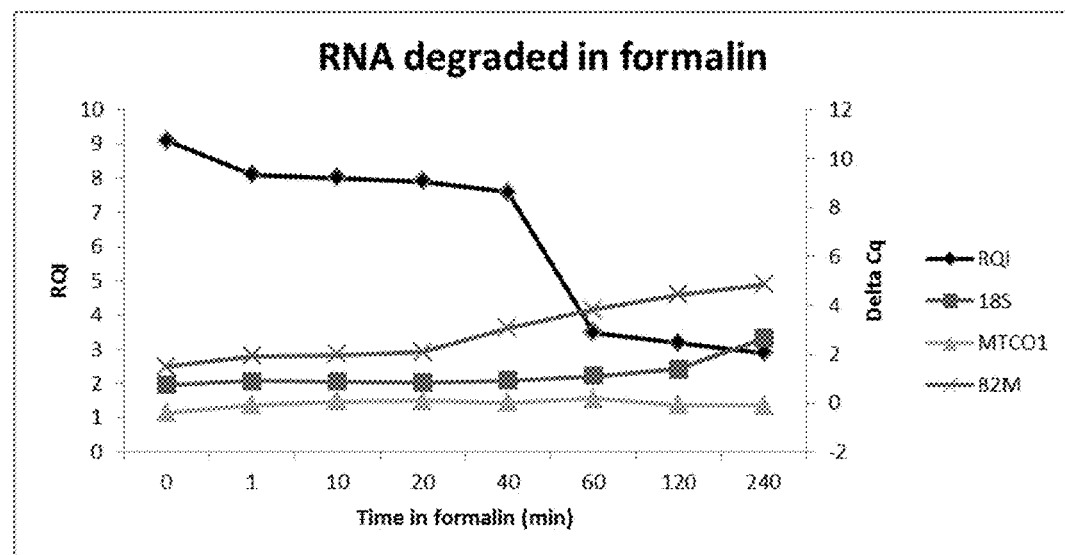

FIG. 11: Degradation of rat RNA in formalin. Degradation measured with the capillary electrophoresis system (Experion, Bio-Rad) and expressed as RQI and with L:S qPCR. The x-axis scale is not linear.

Figure 12:
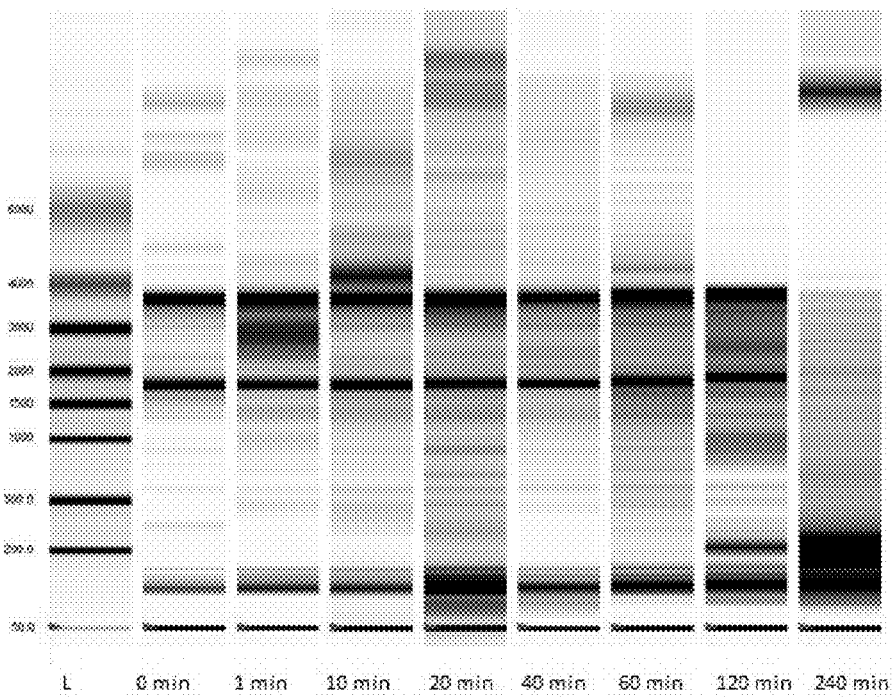

FIG. 12: Gel image derived from the Experion™ System (Bio-Rad) of rat RNA in formalin for different amount of time. The left lane is a molecular size ladder. Intact 28 S RNA appears at 3800 bp and intact 18S RNA appears at 1800 bp.

Figure 13:
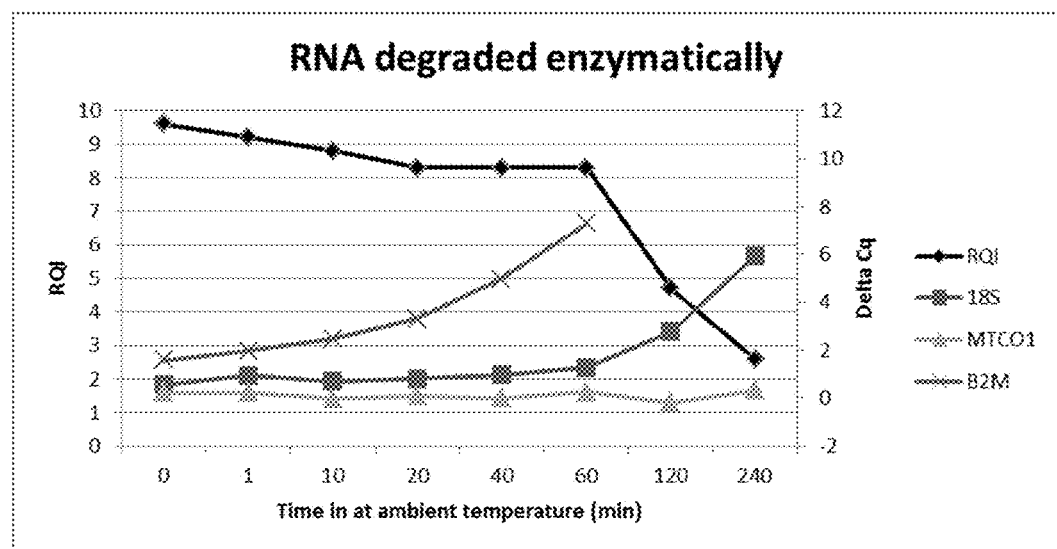

FIG. 13: qPCR analysis of rat RNA degraded enzymatically. Degradation measured with the capillary system (Experion™ System, Bio-Rad) and expressed as RQI and with L:S based on the 18S, MTCO1, and B2M markers. The x-axis scale is not linear.

Figure 14:
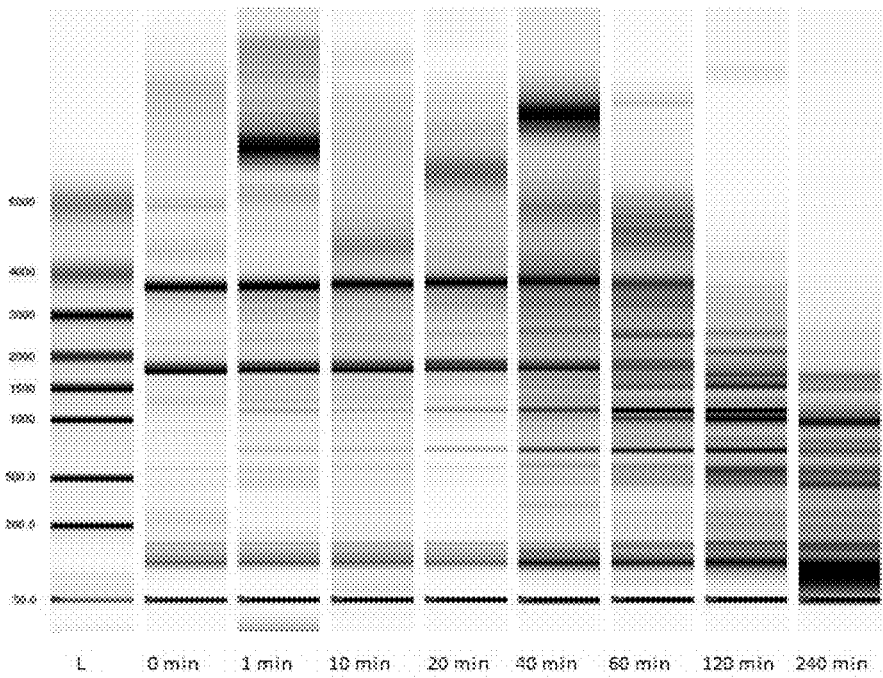

FIG. 14: Gel image of rat RNA degraded enzymatically derived with the Experion™ System (Bio-Rad). The samples were degraded at room temperature for different amount of time. To left lane is a molecular size ladder. Intact 28 S RNA appears at 3800 bp and intact 18S RNA at 1800 bp.

DETAILED DESCRIPTION OF THE INVENTION

The following definitions are set forth to illustrate and define the meaning and scope of various terms used herein.

As used herein, the term "amplicon" refers to a nucleic acid molecule comprising a nucleotide sequence. Particularly, the term "amplicon" refers to a nucleic acid molecule comprising a nucleotide sequence, wherein the nucleic acid molecule was generated by performing an amplification reaction, such as qPCR. The length and the sequence of the nucleic acid molecule are determined by the sequence and the binding sites of the primers used in the amplification reaction. Amplicons according to the description may range in lengths from 20 to 400 bp. Three lengths of amplicons are of importance within the description: Short amplicons (S) shorter than 100 bp, medium length amplicons (M) from 100 to 200 bp, and long amplicons (L) longer than 300 bp.

The term "3'/5' assay" is used herein as known to the expert skilled in the art and refers to the strategy to test integrity of RNA as described in Nolan et al., Nat. Protoc. 1 (2006) 1559-1582 and variations of it that are obvious to a person skilled in the art.

As used herein, the term "cDNA" is used herein refers to a nucleotide sequence complementary or identical to an RNA sequence in either single stranded or double stranded form.

As used herein, the terms "complementary" or "complementarity" are used in reference to polynucleotides related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on, for example, the efficiency and strength of hybridization between nucleic acid strands, amplification specificity, etc.

As used herein, the term "fragment" is used herein refers to a nucleic acid molecule comprising a nucleotide sequence. Particularly, the term "fragment" refers to a nucleic acid molecule comprising a nucleotide sequence, wherein the nucleic acid molecule is a part of a longer native nucleic acid molecule, such as native RNA molecule, typically generated by degradation or cleavage of the native molecule.

The term "gene specific primer" is used herein as known to the expert skilled in the art and refers to a nucleic acid molecule comprising a nucleotide sequence. Particularly, the term "gene specific primer" refers to a synthetic nucleic acid molecule, typically an oligonucleotide of length 7-50 bases, usually predominantly composed of natural deoxyribonucleosides, though ribonucleosides and various synthetic variants such as locked nucleotides (LNA), peptide nucleotides (PNA) and the like may be used in part or fully. The gene specific primer has a sequence that is sufficiently complementary to a sequence in particular RNA molecules to hybridize to it and act as primer for an extension reaction by a suitable polymerase such as a reverse transcriptase.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the Tm of the formed hybrid, and the G:C ratio within the nucleic acids. While the description is not limited to a particular set of hybridization conditions, stringent hybridization conditions are preferably employed. Stringent hybridization conditions are sequence-dependent and will differ with varying environmental parameters (e.g., salt concentrations, and presence of organics). Generally, "stringent" conditions are selected to be about 5° C. to 20° C. lower than the thermal melting point (Tm) for the specific nucleic acid sequence at a defined ionic strength and pH. Preferably, stringent conditions are about 5° C. to 10° C. lower than the thermal melting point for a specific nucleic acid bound to a complementary nucleic acid. The Tm is the temperature (under defined ionic strength and pH) at which 50% of a nucleic acid (e.g., tag nucleic acid) hybridizes to a perfectly matched probe.

The term "mRNA" is used herein as known to the expert skilled in the art and refers to pre-mRNA, pre-mRNA transcripts, mRNA, transcript processing intermediates, mature mRNA used for translation and transcripts from a gene or genes, or nucleic acids derived therefrom. Transcript processing includes processes such as splicing, editing, modifying and degrading. mRNA including samples include, but are not limited to mRNA, mRNA transcripts of the gene or genes, RNA transcribed from amplified DNA, cRNA transcribed from cDNA, DNA amplified from the genes, and the like.

The term "nucleic acid" is used herein as known to the expert skilled in the art and refers to a macromolecule composed of chains of monomeric nucleotides, wherein each nucleotide consists of three components: a nitrogenous heterocyclic base, which is either a purine or pyrimidine; a pentose sugar; and a phosphate group.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "oligo-dT-primer" is used herein as known to the expert skilled in the art and refers to a synthetic oligonucleotide that hybridizes with substantial affinity to an uninterrupted stretch of adenine nucleotides in RNA or DNA. The bases of the oligo-dT-primer as referred to here are composed of essentially only thymine residues that may be deoxyribonucleotides or ribonucleotides (oligo-T-primer) and may contain modified nucleotides, such as LNA and PNA. The oligo-dT-primer may also have one or more anchor nucleotides, i.e., one or several other nucleotides at its 3'-terminal.

As used herein, the term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. The term oligonucleotide may also be used interchangeably with the term "polynucleotide."

The term "polymerase chain reaction" or "PCR" refers to a method for increasing the concentration of a specific segment of a target sequence (amplicon) in a mixture of genomic DNA without cloning or purification. This process for amplifying the target sequence consists of introducing a large excess of two primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment (amplicon) of the desired target sequence. The length of the amplified segment (amplicon) of the desired target sequence is determined by the relative positions of the primers with respect to each other, and therefore, this length is a controllable parameter. With PCR, it is possible to amplify a single copy of a specific target sequence in genomic DNA to a level detectable by several different methodologies known to those skilled in the art. In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded, however in the present description the probes are intended to be single stranded. Probes are useful in the detection, identification and isolation of particular gene sequences.

The term "random primer" or "random sequence primer" is used herein as known to the expert skilled in the art and refers to a primer or a set of primers having a random sequence of 4, 5, 6, 7, 8, 9, 10, 11, 12 or more nucleotides that represent the majority or at least a substantial part of all sequences of that particular length. The term "random sequence" in this context means that the position of alignment and binding of the primer to a target nucleic acid is substantially indeterminate regarding the template under conditions wherein the primer is used to initiate polymerization of a complementary nucleic acid.

The term "reaction mixture" is used herein as known to the expert skilled in the art and refers to an aqueous solution comprising various reagents used for amplification of one or more target nucleic acids, including enzymes, aqueous buffers, salts, primers, target nucleic acid, and nucleoside triphosphates. The mixture can be either a complete or incomplete amplification reaction mixture.

The term "real time PCR", "quantitative PCR" or "qPCR" is used herein as known to the expert skilled in the art and refers to the monitoring of a signal, e.g. a fluorescence signal, emitted from a PCR assay during the reaction as an indicator of amplicon production. The signal increases in direct proportion to the amount of produced amplicon. By measuring this signal increase during each cycle the first significant increase in the amount of produced amplicon can be determined and correlated to the initial amount of target nucleic acid. For emission of the fluorescence signal techniques based on Fluorescence Resonance Energy Transfer (FRET) can be utilized which are well known in the art, e.g. hybridization probes, Taqman probes and molecular beacons.

The term "RNA quality control" is used herein as known to the expert skilled in the art and refers to a quality control method for assessing the initial quality of RNA introduced into analysis usually by reverse transcription followed by a method to quantify DNA such as real-time PCR, microarray hybridization or sequencing or the like. In particular it is assessed if the quantification of RNA by the chosen method is reliable or not, due to the quality of the RNA tested.

The term "RT-qPCR" is used herein as known to the expert skilled in the art and refers to reverse transcription PCR followed by quantitative amplification. RT-qPCR is used to transcribe RNA into complementary DNA (cDNA) under the usage of the enzyme reverse transcriptase. Subsequently, the cDNA is applied to amplification by PCR.

As used herein, the term "sample" is used in its broadest sense. In one sense, it is meant to include a nucleic acid specimen obtained from any source. Biological nucleic acid samples may be obtained from animals (including humans) and encompass nucleic acids isolated from fluids, solids, tissues, etc. Biological nucleic acid sample may also come from non-human animals, including, but are not limited to, vertebrates such as rodents, non-human primates, ovines, bovines, ruminants, lagomorphs, porcines, caprines, equines, canines, felines, ayes, etc. Biological nucleic acids may also be obtained from prokaryotes, like bacteria and other non-animal eukaryotes such as plants. It is contemplated that the present description is not limited by the source of nucleic acids sample, and any nucleic acid from any biological Kingdom finds utility in methods as described herein.

The term "set of primers" is used herein as known to the expert skilled in the art and refers to a group of primers which is required for carrying out an amplification, such as a PCR. The set of primers consists of at least one primer. Furthermore, the set of primers may consist of at least two primers, which specifically bind to two different positions of the nucleic acid template. Two primers flanking a sequence of interest, which is amplified during the amplification reaction, are called forward and reverse primer, respectively. Such forward and reverse primer is also referred to as primer pair. The terms forward and reversed primers are here primarily used for convenience to label the two primers in pair different. The labeling originates from that used in primer design software. The term "set of primers" may also refer to a multitude of different primers, such as random sequence primers. The term may also refer to primers utilized in at least two assays. If two assays according to the description are performed, two forward and two reverse primers are used in order to produce two amplicons. If three assays according to the description are performed, three pairs of primers are used in order to produce three amplicons.

The term "testing RNA" (herein also referred to as "stable RNA") is used herein as known to the expert skilled in the art and refers to RNA that is more resistant to at least some forms of degradation, usually degradation involving RNA nucleases, than average or bulk mRNA. The stable RNA can be chemically different or naturally modified as compared to regular mRNA. In this regard, the testing RNA may comprise a modified or less common 5'-cap structure. Such modification may be $m_3^{2,2,7}$GpppN, $m^7$GpppNm$_{2'-O}$, $m^7$GpppNm$_{2'-O}$pNm$_{2'-O}$p, or γ-methyl-phosphate. Furthermore, the testing RNA may lack the 5'-cap structure. This is the typical case for mRNA synthesized outside the nucleus, such as mitochondrial and chloroplast mRNAs. Also, the testing RNA can comprise a poly-A-tail or the stable RNA can lack the poly-A-tail. Possible are also combinations of the above elements, which are comprised within the stable RNA: i) a modified 5'-cap structure and a poly-A-tail, ii) a modified 5'-cap structure and no poly-A-tail, iii) no 5'-cap structure but a poly-A-tail, iv) no 5'-cap structure and no poly-A-tail. The term "testing RNA" further refers to RNA which can be compartmentalized in the cell to be protected from nucleases. If the stable RNA is not compartmentalized and has a normal 5'-Cap ($5^7$G) it has a modified A-tail or lacks the A-tail completely. Testing mRNA may originate from structural or metabolic genes, which under conditions of inhibited transcription in some cell lines show longest half-lives (Sharova, L. V. et al., DNA Res. 16 (2009) 45-58). The term "testing RNA" particularly refers to RNAs selected from a group of ribosomal RNA, mitochondrial RNA, chloroplast RNA and small nuclear RNA. As described here such stable testing RNA can be mitochondrially encoded cytochrome c oxidase I (MTCO1), also known as cytochrome c oxidase I (COX1), transcript which is less susceptible to degradation by RNases as compared to nucleus encoded mRNA. Other testing RNAs according to the description include ribosomal 18S RNA and the structural U3.

The term "susceptibility" is used herein for characterization of mRNA or RNA regarding its stability against degradation processes. mRNA or RNA with high susceptibility to degradation exhibits a high degree degradation, which means that a pool of mRNA or RNA which was originally present in the cell or tissue is strongly affected by degradation processes leading to extensive fragmentation of the mRNA or RNA molecules. In contrast, mRNA or RNA with low susceptibility to degradation exhibits a low degree of degradation or no degeneration, which means that a pool of mRNA or RNA which was originally present in the cell or tissue is slightly or not affected by degradation processes. As a result, the bulk of mRNA or RNA molecules with low susceptibility within that pool are unaffected by the degradation processes and are thus still present in essentially their original lengths.

The first step in gene expression experiments is the isolation of RNA from a sample. The sample can originate from any organism, such as human, monkey, rabbit, goat, mouse, rat, fish, bacteria, virus, parasite, fungi and can be isolated from the organism but also from other specimens such as but not limited to water, soil, air, scrapes. The sample can be fixed by any crosslinking agent known in the art, such as formalin. In one embodiment the sample is a formalin fixed paraffin embedded (FFPE) sample. Due to the formalin fixation, the samples can exhibit a high degree of RNA degradation. The degradation induced by the formalin fixation can be regarded as physical and/or chemical degradation. During formalin fixation the proteins within the tissue are crosslinked via covalent chemical bonds. Fixation by formalin and other crosslinking substances can also lead to chemical modifications of the RNA that interferes with RT-PCR analysis limiting amplification to short stretches. Such modifications include addition of monomethylol (—CH$_2$—OH) groups to the bases and dimerization. The samples can also be preserved by other means including RNAlater®, RNAstable®, PaxGene® blood or tissue, alcohol, HOPE®, GenTegra™ and the like.

Furthermore, degradation processes can be of physical nature, e.g. degradation induced by UV light, heat or shear forces. Such physical degradation, however, can also be induced by fixation of samples with crosslinking substances. Furthermore, degradation processes can be of enzymatic nature, e.g. degradation induced by nucleases, typically ribonucleases (also called RNases), which can be exoribonucleases such as RNase A, RNase H, RNase I, RNase III, RNase L, RNase P, RNase PhyM, RNase T1, RNase T2, RNase U2, RNase V1, RNase V or endoribonucleases PNpase, RNase PH, RNase II, RNase R, RNase D, RNase T, oligoribonuclease, exoribonuclease I and exoribonuclease II. For more comprehensive list see http://www.chem.qmul.ac.uk/iubmb/enzyme/EC3/1/or http://www.ebi.ac.uk/intenz/query?cmd=SearchEC&ec=3.1. Notably, the nucleases degrading the RNA can originate from the sample studied but can also come externally.

The above explained degeneration processes lead to unreliable and inaccurate results in gene expression analysis performed using qPCR. Therefore, assessing the quality of the RNA within a sample in general, especially in a fixed sample is essential. One aspect of the description is a method to assess RNA quality in a sample for more reliable and accurate results in gene expression analysis. The method comprises the steps of preparing cDNA from RNA present in the sample, quantifying by amplification at least one amplicon of a first cDNA in the sample, wherein the first cDNA derives from mRNA, quantifying by amplification at least one amplicon of a second cDNA, wherein the second cDNA derives from stable RNA, assessing the quality of the mRNA in the sample by comparing the amount of the at least one amplicon of the first cDNA with the amount of the at least one amplicon of the second cDNA, wherein the stable RNA used to produce the second cDNA has low susceptibility to nuclease degradation. These steps are basically used for assessing the grade of degradation caused by enzymes, such as nucleases. The mRNA to be analyzed or mRNA, from which information on the grade of degradation can be extrapolated to the mRNA to be analyzed, is compared to the stable RNA not affected by enzymatic degradation.

As mentioned above, the method comprises the step of preparing cDNA from RNA present in the sample. The RNA molecules present in a sample are converted into cDNA by reverse transcription. Within the method described herein, the conversion of RNA present in the sample into cDNA is performed, i.e. the conversion by reverse transcriptase leads to the production of a pool of cDNA molecules reflecting a part of or all RNA molecules present in the sample. In one embodiment the reverse transcription can be performed with any of the methods known in the art, such as methods using random sequence primers, oligo-dT-primers, sequence specific primers or a mixture thereof. In another embodiment, a mixture of random sequence primers and oligo(dT) primers may be used producing cDNA at higher yield. In one embodiment the length of the random sequence primers can vary from 4 to 20 nucleotides. In a specific embodiment the length of the random sequence primers can vary from 5 to 10 nucleotides. In a more specific embodiment the length of the random sequence primers is exactly 6 nucleotides. All reagents which are necessary to perform reverse transcription such as buffers, primers and desoxynucleotides are well known in the art. Furthermore, an optimization of concentrations used in the context of the present description can be obtained through routine experimentation.

The step of preparing cDNA from RNA present in the sample is followed by quantifying by amplification at least one amplicon of a first cDNA in the sample, wherein the first cDNA derives from mRNA, and quantifying by amplification at least one amplicon of a second cDNA, wherein the second cDNA derives from stable RNA. In one embodiment, at least one of the primers used for the reverse transcription described above is identical to at least one of the primers used for the amplification of the at least one amplicon of the second cDNA. This strategy is particularly advantageous in 1-step RT-qPCR protocols. Separately from quantifying by amplification at least one amplicon of a first and at least one amplicon of a second cDNA and assessing the quality as described above, the following additional steps may be performed optionally: quantifying by amplification at least two amplicons of the second cDNA and assessing the quality of the stable RNA in the sample by comparing the amounts of the at least two amplicons of the second cDNA. Particularly advantageous is the use of three amplicons which are amplified from the second cDNA. In the additional steps the at least two or three amplicons can originate from adjacent or overlapping sequences of the second cDNA. By comparing the amount of the at least two or three amplicons in at least two or three assays, the grade of degradation of the second cDNA can be assessed. The partial degradation assessed here is mainly caused by chemical and/or physical degradation.

In one embodiment, the mRNA derives from a gene with an expression that is essentially invariant of the treatment studied. In a specific embodiment, the mRNA derives from Alu repeats. In another embodiment, the mRNA and the stable RNA derives from a gene with an expression that is essentially invariant of the treatment studied. Hence, a good candidate for the normal mRNA as reference is one or more of the reference genes used in the study, since the criterion when selecting reference gene is their expression should be stable, hence invariant of the treatment studied.

One aspect of the present description is a method for assessing RNA quality for qPCR experiments. This can be performed by comparing the amplification of two different RNAs. One of these RNAs may be a normal mRNA with 5'-cap and 3'-A-tail to have normal sensitivity towards nucleolytic digestion (herein referred to as "mRNA"), while the second RNA shall be different from normal mRNAs to be less susceptible to nucleolytic degradation. For example, the second RNA (testing RNA) may be metabolic RNA, structural RNA, mitochondrial RNA or chloroplast RNA. The RNA may lack 5'-cap or may have a different 5'-cap and/or lacks 3'-A-tail or have a different A-tail. In one embodiment, the stable RNA may comprise a modified 5'-cap structure or may lack the 5'-cap structure. In one embodiment, the stable RNA may comprise a poly-A-tail or may lack the poly-A-tail. In one embodiment the stable testing RNA may comprise a modified 5'-cap structure and a poly-A-tail. In one embodiment the stable RNA may lack the 5'-cap structure and may lack the poly-A-tail. In another embodiment the stable RNA may comprise a modified 5'-cap structure or may lack the 5'-cap structure. In another embodiment, the stable RNA may lack the modified 5'-cap structure and may comprise a poly-A-tail.

The stable RNA which shall be used as testing RNA can also be compartmentalized in the cell to be protected from nucleases. Various types of RNA were tested and it was unexpectedly found that the stable RNA for mitochondrially encoded cytochrome c oxidase I (MTCO1), also known as cytochrome c oxidase I (COX1), to be particularly less susceptible to degradation. Notably, MTCO1 stable RNA is mitochondrially transcribed, thus compartmentalized, and it lacks the normal 5'-Cap structure and 3' A-tail. In one embodiment, the stable RNA is a mitochondrial RNA. In a specific embodiment the mitochondrial RNA is MTCO1. In another specific embodiment, the stable RNA is a chloroplast RNA.

Other stable RNAs that can be used as testing RNA include ribosomal RNAs and small nuclear RNAs. Among these, the structural U3 RNA has been identified to be particularly stable and useful for the present inventive method. The very extensive or even complete degradation of mRNA in a sample is assessed by comparing the amplification of the stable RNA with normal mRNA as reference. Thus, in one embodiment, the stable RNA is structural U3.

In one embodiment, the mRNA derives from a gene with an expression that is essentially invariant of the physiological status of the cell, in particular when changes of the physiological status of a cell due to different drug treatment methods are studied. In one embodiment, the mRNA derives from Alu repeats. In another embodiment, the mRNA and the testing RNA derives from a gene with an expression that is essentially invariant of the treatment studied. Hence, a good candidate for the normal mRNA as reference is one or more of the reference genes used in the study.

Thus, the present description provides in general improved methods for the quality control of RNA used as a starting material for PCR and qPCR experiments. The improvement is based on the fact that the assay for assessing the quality is performed using cDNA generated from RNA by reverse transcription, wherein the RNA is less susceptible to degradation processes.

Partial degradation of mRNA can be assessed by amplifying a target cDNA with multiple assays. In one embodiment, degradation of mRNA can be assessed by amplifying a target cDNA with two assays, i.e. quantifying by amplification two amplicons of a cDNA. In one embodiment, degradation of mRNA can be assessed by amplifying a target cDNA with three assays, i.e. quantifying by amplification three amplicons of the cDNA. It is not important what region of the cDNA the assays amplify and produce the amplicons from; a particular assay may or may not be located 5' of any other. Independent therefrom, the assays shall result in amplicons that differ in length and they shall have similar PCR efficiencies. A minimum of two assays is needed, however, three assays provide a more accurate assessment of RNA quality. In one embodiment, the amplicon lengths for the at least two amplicons produced in the two assays are for the short amplicon <100 bp and for the long amplicon at least 100. In one embodiment, the amplicon lengths for the at least two amplicons produced in the two assays are for the short amplicon <100 bp and for the long amplicon 100-200 bp. In one embodiment, the amplification of the at least two amplicons is performed using one common primer for the at least two amplicons. In one embodiment, the amplicon lengths for the three amplicons produced in the three assays are for the short amplicon (S)<100 bp, for the medium amplicon (M) 100-200 bp and for the long amplicon (L)>300 bp. In one embodiment, the amplification of the three amplicons is performed using one common primer. The shorter amplicon sequences are thus encompassed by the longer, which reduces any amplification bias. In difference from the method known in the art described in WO 2005/090609, which teaches the generation of multiple amplicons from the same reporter, where lower yield of the amplicon closer to the mRNA 5' end indicates more degraded RNA, in this more degraded RNA is indicated by lower yield of the long amplicon relative to the short amplicon essentially independently of their locations on the mRNA.

In one embodiment, the two or three assays described in the previous paragraph are performed on stable testing RNA, such as metabolic RNA, structural RNA, mitochondrial RNA or chloroplast RNA. In one embodiment, the two or three assays are performed on mitochondrial RNA. In one embodiment, the two or three assays are performed on MTCO1. In another embodiment, the two or three assays are performed on structural U3 RNA.

The integrity of mRNA is assessed by comparing the yields of the three assays, for example if qPCR is used, by comparing $\Delta Cq_{LM}=Cq_L-Cq_M$ and $\Delta Cq_{MS}=Cq_M-Cq_S$, where Cq is the number of amplification cycles needed to reach a particular threshold fluorescence level in qPCR. By performing two comparisons based on three amplicons results in much wider dynamic range than performing a single comparison possible with only two different length amplicons. The targeted mRNA should be abundant, preferably highly abundant to produce reliably Cq measurements even for very degraded samples. In fact, the more abundant target the better.

The differential yield of amplicons of different lengths produced from the same RNA does not reflect degradation beyond the length of the shortest amplicon. Hence, degradation by mechanisms that digest the RNA into very short fragments, as many nucleases do, is not sensed by this strategy.

RNA quality is assessed in the sample by comparing the amount of the amplicon of the first cDNA deriving from mRNA with the amount of the amplicon of the second cDNA deriving from stable RNA. In one embodiment, this comparison is performed using the geometric mean expression of multiple mRNAs. This averages out random variation in the reference genes' expressions providing under some conditions a more stable norm. RNA quality can also be assessed in the sample by comparing the amount of the amplicon of the first cDNA deriving from mRNA with the amount of the amplicon of the second cDNA deriving from stable testing RNA, wherein the mRNA is transcribed from Alu repeats in the human genome. In this case the first cDNA is generated with primers amplifying the Alu repeats in the human genome which is a very common sequence in the transcriptome. Expression of genes producing transcripts that encompass the common sequence may be regarded to be invariant of treatment, as due to the very large number of such transcripts their overall expression is usually reasonably invariant of treatment and a suitable norm.

Samples not modified actively upon collection by e.g. fixation, embedding, stabilization etc., will undergo spontaneous degradation and decay of RNA. This is demonstrated in Example 1 on liver tissue. The degree of amplification of a stable RNA with that of a normal mRNA changes with time. This reflects the degree of mRNA degradation, which under any given conditions reflects the length of the degradation process. Hence, upon injury, stabbing, mutilation or death that causes a piece of bodily tissue or fluid to start decomposing and degrading its RNA, the time of death can be assessed though the degree of RNA degradation that has occurred.

A further aspect of the new invention is a kit for RNA quality control, wherein the kit comprises a first set of primers for preparing cDNA from RNA present in a sample, a second set of primers for the amplification of at least one amplicon of a first cDNA in the sample, wherein the first cDNA derives from mRNA, a third set of primers for the amplification of the at least one amplicon of a second cDNA, wherein the second cDNA derives from a comparatively stable testing RNA, said testing RNA being selected from a group consisting of ribosomal RNA, mitochondrial RNA, chloroplast RNA and small nuclear RNA wherein the testing RNA used to produce the second cDNA has low susceptibility to nuclease degradation.

In one embodiment, the set of primers comprises random sequence primers, oligo-dT-primers, sequence specific primers or a mixture thereof. In one embodiment, a mixture of random sequence primers and oligo(dT) primers may be comprised in the kit. In one embodiment the lengths of the random sequence primers can vary from 4 to 20 nucleotides. In another embodiment the lengths of the random sequence primers can vary from 5 to 10 nucleotides. In another embodiment the length of the random sequence primers is exactly 6 nucleotides. All reagents which are necessary to perform reverse transcription such as buffers, primers and desoxynucleotides may be comprised in the kit according to the present description.

In one embodiment, at least one of the primers or set of primers comprised in the kit and used for reverse transcription is identical to at least one of the primers or set of primers used for the amplification of at least one amplicon of the second cDNA. In one embodiment, the second set of primers specifically binds within a gene with an expression that is essentially invariant of the treatment studied. In a specific embodiment, the second set of primers specifically binds within Alu repeats.

In one embodiment, the third set of primers is suitable for the amplification of at least one amplicon of the second cDNA, wherein the second cDNA derives from a testing RNA which is a comparatively stable RNA. Therefore, the primers specifically bind within the second cDNA deriving from stable RNA, such as, ribosomal RNA, mitochondrial RNA, chloroplast RNA, or small nuclear RNA such as U3. In one embodiment, the third set of primers is suitable for the amplification of at least one amplicon of the second cDNA, wherein the second cDNA derives from the mitochondrial MTCO1. In another embodiment, the testing RNA may be ribosomal 18S RNA and the structural U3.

In one embodiment, the kit comprises a set of primers for performing at least two assays. In one embodiment, the two assays produce a short amplicon with a length of <100 bp and a long amplicon with a length of at least 100. In one embodiment, the amplicon lengths for the at least two amplicons produced in the two assays are for the short amplicon <100 bp and for the long amplicon 100-200 bp. In one embodiment, the amplification of the at least two amplicons is performed using one common primer for the at least two amplicons. In one embodiment, the amplicon lengths for the three amplicons produced in the three assays are for the short amplicon (S)<100 bp, for the medium amplicon (M) 100-200 bp and for the long amplicon (L)>300 bp. In one embodiment, the amplification of the three amplicons is performed using one common primer for the three amplicons.

Further embodiments are included by the following items:
1. A method to assess RNA quality in a sample, the method comprising the steps of
   a) preparing cDNA from RNA,
   b) quantifying by amplification at least one amplicon of a first cDNA, wherein the first cDNA derives from mRNA,
   c) quantifying by amplification at least one amplicon of a second cDNA, wherein the second cDNA derives from a testing RNA, said testing RNA selected from a group consisting of ribosomal RNA, mitochondrial RNA, chloroplast RNA and small nuclear RNA,
   d) assessing the quality of the mRNA by comparing the amount of the at least one amplicon of the first cDNA with the amount of the at least one amplicon of the second cDNA.
2. The method of item 1, wherein optionally the additional steps are performed:
   e) quantifying by amplification separately from steps b) to d) at least two amplicons of the second cDNA,
   f) assessing the quality of the testing RNA by comparing the amounts of the at least two amplicons of the second cDNA.
3. The method of item 1-2, wherein the mRNA derives from a gene with an expression that is essentially invariant of the physiological status of a cell.
4. The method of item 1-3, wherein the mRNA comprises Alu repeats.
5. The method of item 1-4, wherein the comparison of step d) is performed using the geometric mean expression of multiple mRNAs.
6. The method of item 1-5, wherein the amplification of the at least two amplicons of step e) is performed using one common primer for the at least two amplicons.
7. The method of items 1-6, wherein at least one of the primers used in step a) is identical to at least one of the primers used in step c).
8. The method of items 2-7, wherein the first of the at least two amplicons of step e) has a length of less than 100 bp and wherein the second of the at least two amplicons of step e) has a length of at least 100 bp.
9. A kit for assessing RNA quality in a sample, the kit comprising the following elements:
   a) a first set of primers for preparing cDNA from RNA,
   b) a second set of primers for the amplification of at least one amplicon of a first cDNA, wherein the first cDNA derives from mRNA,
   c) a third set of primers for the amplification of at least one amplicon of a second cDNA, wherein the second cDNA derives from a testing RNA, said testing RNA selected from a group consisting of ribosomal RNA, mitochondrial RNA, chloroplast RNA and small nuclear RNA.
10. The kit of item 9, wherein the first set of primers comprises random sequence primers, oligo-dT-primers, sequence specific primers or a mixture thereof.
11. The kit of items 9-10, wherein the second set of primers specifically binds within a gene with an expression that is essentially invariant of the physiological status of a cell.
12. The kit of items 9-11, wherein the second set of primers specifically binds within Alu repeats.
13. The kit of items 9-12, wherein the third set of primers is designed such that at least two amplicons are amplified, the first of the at least two amplicons has a length of less than 100 bp and wherein the second of the at least two amplicons has a length of at least 100 bp.
14. The kit of item 13, wherein the amplification of the at least two amplicons is performed using one common primer.
15. The kit of items 9-14, wherein at least one of the primers of the first set of primers is identical to at least one of the primers of the third set of primers.

For performing qPCR, different detection formats are known in the art. The below mentioned detection formats provide an easy and straight forward possibility for gene expression analysis:

a) TaqMan Hydrolysis Probe Format:

A single-stranded Hybridization Probe is labeled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3' exonuclease activity of the Taq Polymerase during the subsequent elongation phase. As a result the excited fluorescent component and the quencher are spatially separated from one another and thus a fluorescence emission of the first component can be measured. TaqMan probe assays are disclosed in detail in U.S. Pat. Nos. 5,210,015, 5,538,848, and 5,487,972. TaqMan hybridization probes and reagent mixtures are disclosed in U.S. Pat. No. 5,804,375.

b) Molecular Beacons:

These hybridization probes are also labeled with a first component and with a quencher, the labels preferably being located at both ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118,801).

c) FRET Hybridization Probes:

The FRET Hybridization Probe test format is especially useful for all kinds of homogenous hybridization assays (Matthews, J. A., and Kricka, L. J., Analytical Biochemistry 169 (1988) 1-25). It is characterized by two single-stranded hybridization probes which are used simultaneously and are complementary to adjacent sites of the same strand of the amplified target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected. Alternatively to monitoring the increase in fluorescence of the FRET acceptor component, it is also possible to monitor fluorescence decrease of the FRET donor component as a quantitative measurement of hybridization event.

In particular, the FRET Hybridization Probe format may be used in real time PCR, in order to detect the amplified target DNA. Among all detection formats known in the art of real time PCR, the FRET-Hybridization Probe format has been proven to be highly sensitive, exact and reliable (WO 97/46707; WO 97/46712; WO 97/46714). As an alternative to the usage of two FRET hybridization probes, it is also possible to use a fluorescent-labeled primer and only one labeled oligonucleotide probe (Bernard, P. S., et al., Analytical Biochemistry 255 (1998) 101-107). In this regard, it may be chosen arbitrarily, whether the primer is labeled with the FRET donor or the FRET acceptor compound.

d) SybrGreen Format:

It is also within the scope of the description, if real time PCR is performed in the presence of an additive according to the description in case the amplification product is detected using a double stranded nucleic acid binding moiety. For example, the respective amplification product can also be detected according to the description by a fluorescent DNA binding dye which emits a corresponding fluorescence signal upon interaction with the double-stranded nucleic acid after excitation with light of a suitable wavelength. The dyes SybrGreenI and SybrGold (Molecular Probes) have proven to be particularly suitable for this application. Intercalating dyes can alternatively be used. However, for this format, in order to discriminate the different amplification products, it is necessary to perform a respective melting curve analysis (U.S. Pat. No. 6,174,670).

The following examples 1-8 are provided to aid the understanding of the present description, the true scope of which is set forth in the appended claims. It is understood that modifications can be made in the procedures set forth without departing from the spirit of the description.

EXAMPLE 1

Differential Stability of RNAs in Tissue Decomposing at Ambient Temperature

Figure 1B:
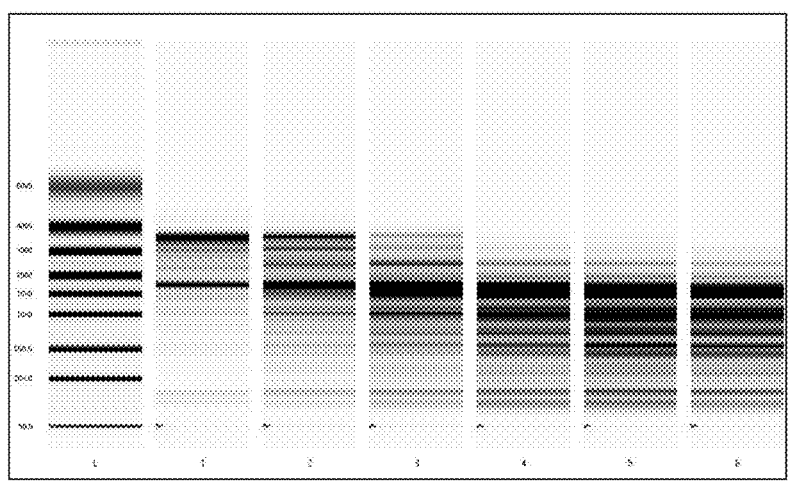
Figure 1C:
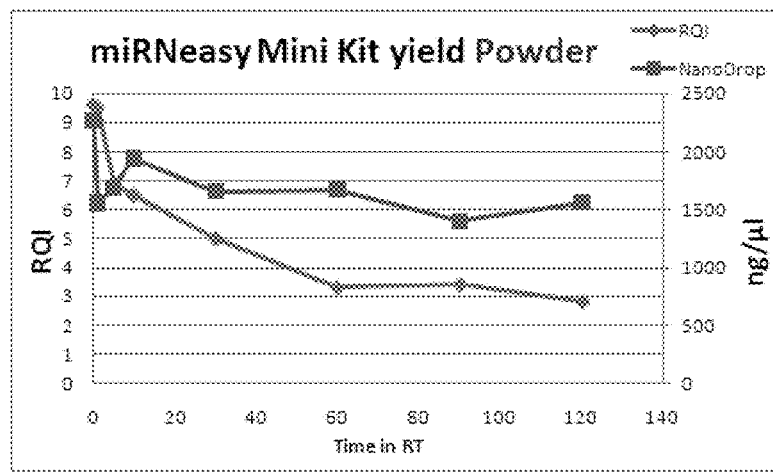
Figure 1D:
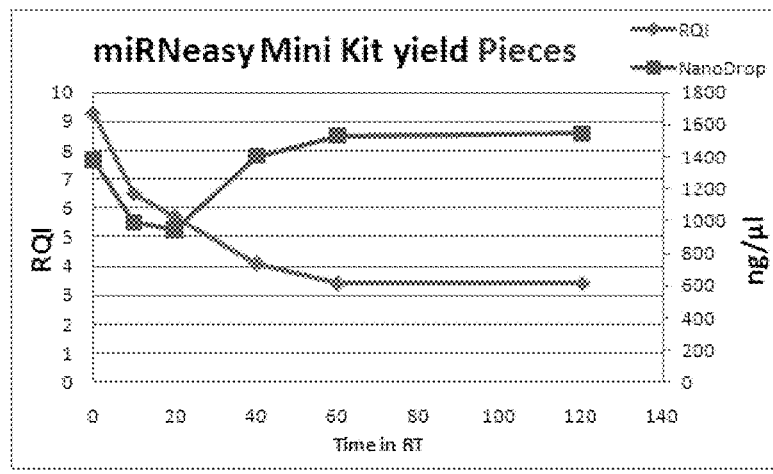
Figure 1E:
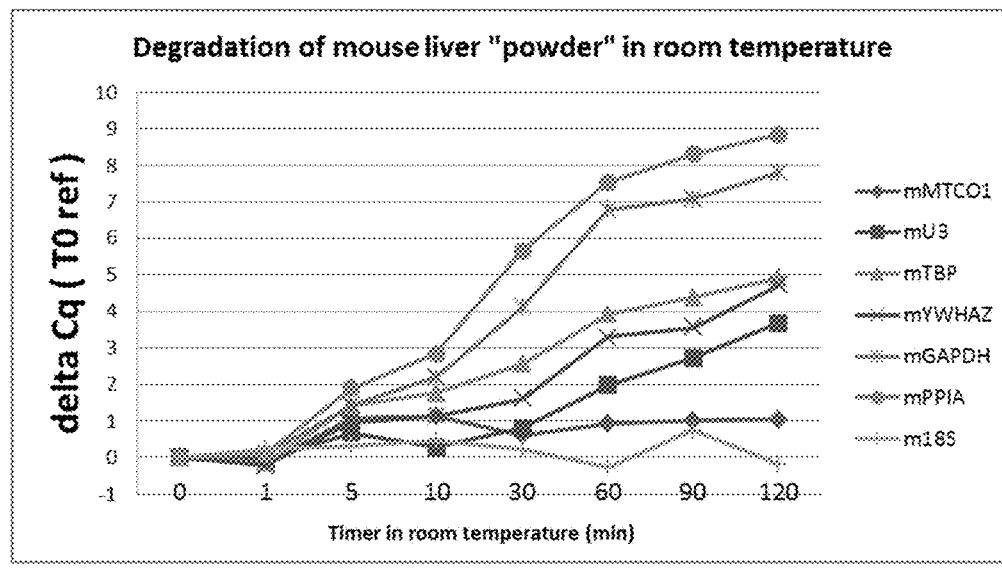
Figure 1F:
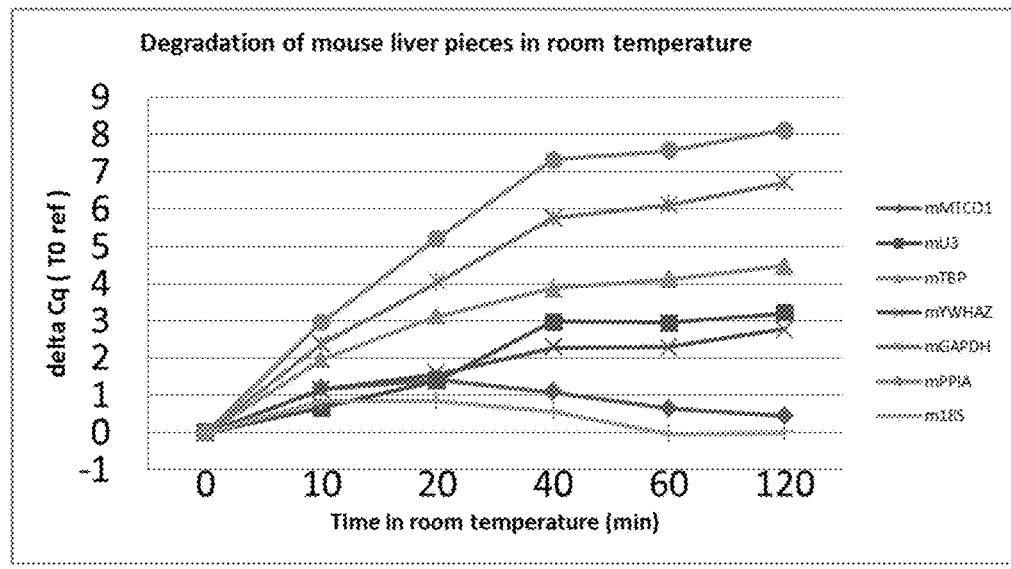

Fresh liver was collected from sacrificed mice. One part of the mouse liver was cut into pieces and immediately frozen in liquid nitrogen to prevent any degradation before the start of a controlled experiment. One piece of the liver was taken out at a time left at ambient temperature for 0, 10, 20, 40, 60 or 120 minutes, where after the RNA was extracted. These data are henceforth referred to as pieces of liver. One part of the frozen liver was placed in a mortar filled with the liquid nitrogen and grounded into powder. Also the liver powder was taken out from the liquid nitrogen and left at ambient temperature for 0, 1, 5, 10, 30, 60, 90 and 120 minutes, where after the RNA was extracted. The RNA was analyzed by capillary electrophoresis with the Bio-Rad Experion. The electropherogram traces are dominated by the ribosomal RNAs and show their degradation with time, reflected by the disappearance of the two intense slow migrating bands dominating at 0 minutes and the appearance of a manifold of fast migrating bands giving a smeary appearance at later times (FIGS. 1A and 1B). Analysis of the traces using the Experion™ software to calculate the RNA Quality Index (RQI) shows RQI decreases steeply with time during at least 60 minutes, where after RQI levels off at a value between 3 and 4 (FIGS. 1C and 1D). The samples were also analyzed spectroscopically using the Nanodrop. The measured absorption does fluctuate a little but it is not systematic and there is no trend (FIGS. 1C and 1D). Clearly, the Nanodrop absorption measurements do not reflect RNA quality. The degradation of individual RNAs in the samples was measured with RT-qPCR (FIGS. 1E and 1F). The following primer sequences were used for mouse assays:

```
MTCO1:
                                    (SEQ ID NO: 1)
    Forward: ATGAAACCCCCAGCCATAAC (SEQ ID NO: 2)
    Reverse: GGTGCCCAAAGAATCAGAAC U3:
                                    (SEQ ID NO: 3)
    Forward: TGTAGAGCACCCGAAACCAC (SEQ ID NO: 4)
    Reverse: CCAAAGGAGGGAAGAACGA
```

-continued

TBP:
Forward: GGAATTGTACCGCAGCTT (SEQ ID NO: 5)

Reverse: ACGAAGTGCAATGGTCTTTA) (SEQ ID NO: 6)

YWHAZ:
Forward: TTCCCAGCCTTAAAAGGTCT (SEQ ID NO: 7)

Reverse: GGCTGCTCACAGGCTA (SEQ ID NO: 8)

GAPDH:
Forward: TGTTTGTGATGGGTGTGAAC (SEQ ID NO: 9)

Reverse: TGGGTGGCAGTGATGG (SEQ ID NO: 10)

PPIA:
Forward: TCCTAAAGCATACAGGTCCT (SEQ ID NO: 11)

Reverse: AGACCACATGCTTGCCA (SEQ ID NO: 12)

18S:
Forward: GTGTGCCTACCCTGCG (SEQ ID NO: 13)

Reverse: ACTTACTGGGAATTCCTCGT (SEQ ID NO: 14)

For most RNAs the Cq values increase with time, reflecting reduction in the amount of amplifiable material caused by degradation. Most surprisingly, exceedingly large variation in the degradation kinetics of the different RNAs was observed. While the measured amount of some mRNAs decreases by more than 99% (Cq increases by more than 7 cycles), the amounts of other RNAs are virtually unaffected. Even more surprisingly, in fact, totally unexpected is our finding that the most stable RNAs are chemically different from normal mRNAs and/or are compartmentalized, in particular located in the mitochondria within the cell; the most stable RNAs in our study are: 18S, MTCO1 (mitochondrial cytochrome oxidase subunit 1), and U3.

EXAMPLE 2

Probing RNA Degradation with the Invented Markers and Determining the Time of Death Using the model system based on mouse liver as already described in Example 1, the extracted amounts of MTCO1 and U3 after various incubation times at ambient temperature were measured with RT-qPCR (FIG. 2A). The Cq values, reflecting the amounts of amplifiable cDNA produced from the RNA, change very little with time. The MTCO1 Cq stays most surprisingly at the same level throughout the entire degradation period of 120 minutes. The variation of the measured $Cq_{MTCO1}$ over time is very low. For U3 Cq does increase moderately with time, evidencing some, though limited degradation.

The very surprising observation that some unusual RNAs, in particular MTCO1, are virtually resistant to degradation induced by conditions such as being left at ambient temperature after freeze-thawing makes it possible to assess the integrity and quality of RNA in a sample using the methods taught here by comparing the amount of a stable RNA, such as the MTCO1, and a regular mRNA. Such comparison with the common reference genes TBP, YWHAZ, and GAPDH is shown in FIG. 2B. The data are presented as differences in Cq values normalized to 0 at time 0 before the onset of degradation. In all comparisons the difference between Cq values of the normal mRNA and the MTCO1 according to the present description increases with time smoothly throughout the studied time interval reaching differences of 4-7 cycles. This corresponds to 16-634 fold difference. This evidences superior stability of MTCO1 compared to the reference genes and demonstrate the suitability to assess and monitor RNA degradation according to the present description. Reciprocally, determining the degree of RNA degradation we can estimate how long the tissue has been decomposing. In events decomposition was initiated by injury or death the time of causing injury or death can be estimated from the degree of degradation based on the present disclosure.

FIG. 2C compares MTCO1 with another reference gene, PPIA, and with the structural 18S RNA. Comparison of MTCO1 and PPIA clearly reflects mRNA degradation, while comparison with 18S shows very little variation. Clearly, as taught herein comparison of MTCOI or other stable non-mRNA, with a reference mRNA reflects integrity of the mRNAs in a sample.

EXAMPLE 3

Probing of RNA Integrity with the Present Description Compared to Capillary Electrophoresis as Taught in the Art The system described already in Examples 1 and 2 based on liver left to decompose at ambient temperature is used. The RNA integrity assessed is compared to RNA integrity assessed by capillary electrophoresis using the Bio-Rad Experion, which is currently state of the art technique, in FIG. 3. The present description demonstrates assessing RNA quality by comparing amounts of MTCO1 and PPIA measured with qPCR. Correlation is clear: as the standard index RQI decreases the measured ratio MTCOI to PPIA according to the present description, increases, evidencing MTCO1 becoming more abundant than PPIA as RNA generally degrades. Most evidently and interestingly the slope of RQI versus the measured MTCO1/PPIA expression ratio as taught here decreases with increasing time, evidencing that the invented method here is more sensitive to RNA degradation than the state of the art analysis of RNA by capillary electrophoresis. For extensively degraded DNA the RQI levels off around a value of 3, while the MTCO1/ref gene expression ratio measured according to the present description continues to increase reflecting further degradation that is not sensed by the state of the art capillary electrophoresis.

EXAMPLE 4

Assessing RNA Degradation Induced by Heat

A pool of human RNA (70 ng/µl) was heated in a 1.5 ml Eppendorf tube to 95° C. 10 µl samples were collected at 0, 1, 10, 20, 40 and 60 minutes for analysis with capillary electrophoreses in the Experion™ and with RT-qPCR. FIG. 4 shows electrophoretic traces measured with the Experion. The gradual degradation of ribosomal RNA with time is clearly reflected by the disappearance of two dominant slowly migrating bands and the appearance of fast migrating smear.

According to the present description three qPCR assays that amplify 18S RNA were designed with the following primers:

```
Primers for Assay Long (L), amplicon length
299 bp:
                                       (SEQ ID NO: 15)
Forward: GAGACTCTGGCATGCTAACT (SEQ ID NO: 16)
Reverse: GGACTTAATCAACGCAAGCT Primers for Assay Medium (M), amplicon length
100:
                                       (SEQ ID NO: 17)
Forward: GTTGAACCCCATTCGTGATG (SEQ ID NO: 18)
Reverse: GGACTTAATCAACGCAAGCT Primers for Assay Short (S), amplicon length
74 bp:
                                       (SEQ ID NO: 19)
Forward: GGGGATTGCAATTATTCCCC (SEQ ID NO: 20)
Reverse: GGACTTAATCAACGCAAGCT
```

Figure 5A:
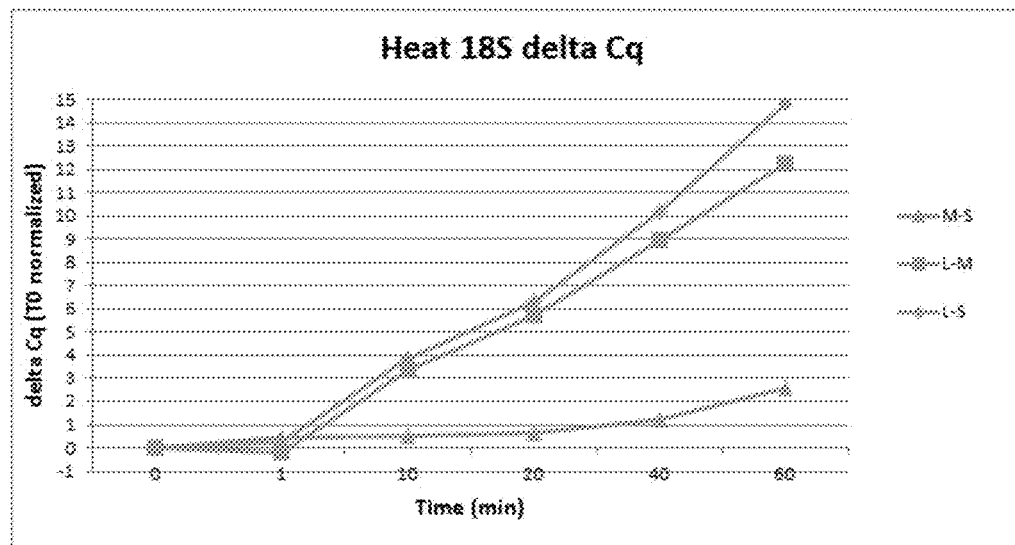
Figure 5B:
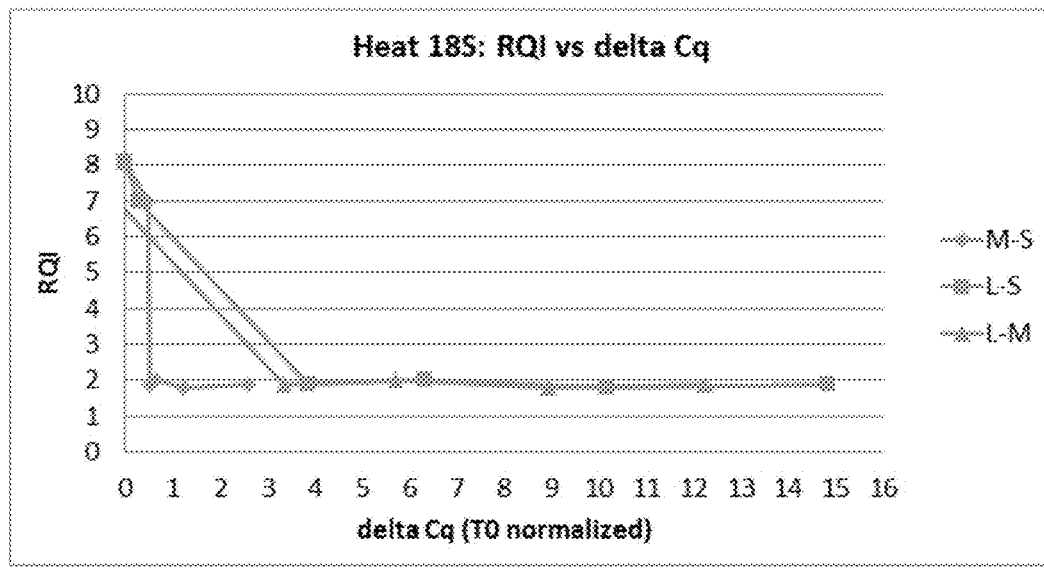

The amount of PCR product produced by the M assay relative to the L assay (M:L), S assay relative to L assay (S:L), and the S assay relative to the M assay (S:M) are shown in FIG. 5A. The ratios M:L and S:L increase dramatically with extended heating evidencing much higher yields of the M and S assays relative to the L assay, reflecting degradation of RNA, most likely into fragments. Also the S:M ratio increases with extended heating. Here the change is initially moderate, but the degree of change increases as the degradation proceeds. This suggest that the S:M ratio is not very sensitive to the initial phase of the degradation, when the fragments are still rather long, but as degradation becomes more extensive the changes are sensitively reflected by the S:M ratio. Clearly, the S:M ratio is more sensitive to reflect extensive degradation than the M:L ratio. FIG. 5B compares the sensitivities of current state of the art measurement of RNA quality by capillary electrophoreses quantified as RQI with measurements of expression ratios according to the present description on the heat induced RNA degradation. It is seen that the initial phase of degradation reflected by RQI dropping from about 8 to 2 both methods sense the changes. While the RQI drops abruptly, most likely reflecting high impact on the ribosomal RNAs that dominate the electropherogram, the measured amplicon ratios as disclosed by the present description, increase gradually reflecting much higher sensitivity to the degree of RNA integrity. Once RQI reaches a value about 2 it does not change meaningfully anymore, while the amplicon ratios continue to decrease reflecting the ongoing additional degradation of the mRNAs that is obviously not sensed by the RQI.

The RNA was also analyzed using B2M as marker for the here invented method to assess mRNA quality by measuring different length amplicons. The following primers were used:

```
Primers for Assay Long (L), amplicon length
342 bp:
                                       (SEQ ID NO: 21)
Forward: GTTTACTCACGTCATCCAGC (SEQ ID NO: 22)
Reverse: GCAAGCAAGCAGAATTTGGA Primers for Assay Medium (M), amplicon length
145 bp:
                                       (SEQ ID NO: 23)
Forward: AAAAGATGAGTATGCCTGCC (SEQ ID NO: 24)
Reverse: GCAAGCAAGCAGAATTTGGA Primers for Assay Short (S), amplicon length
81 bp:
                                       (SEQ ID NO: 25)
Forward: GATCGAGACATGTAAGCAGC (SEQ ID NO: 26)
Reverse: GCAAGCAAGCAGAATTTGGA
```

Figure 5C:
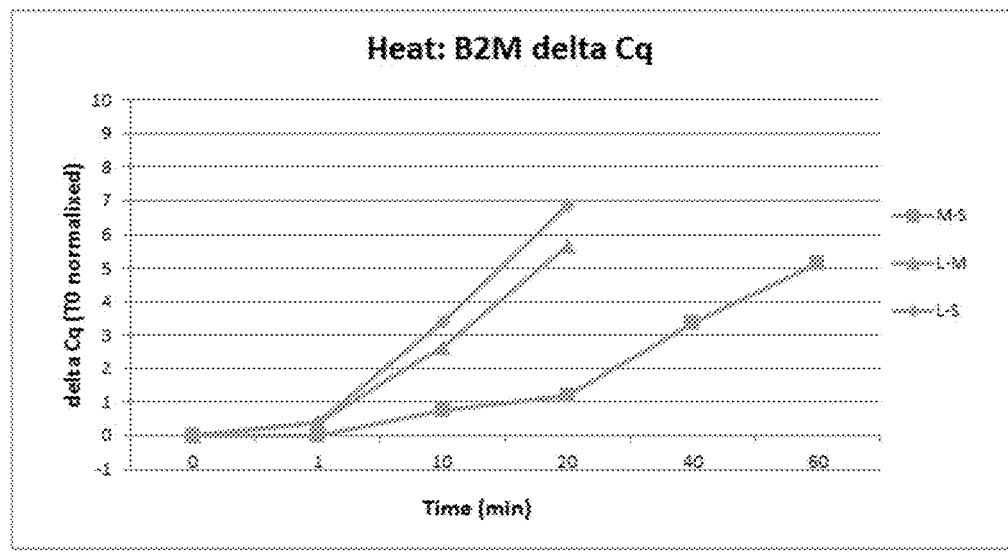
Figure 5D:
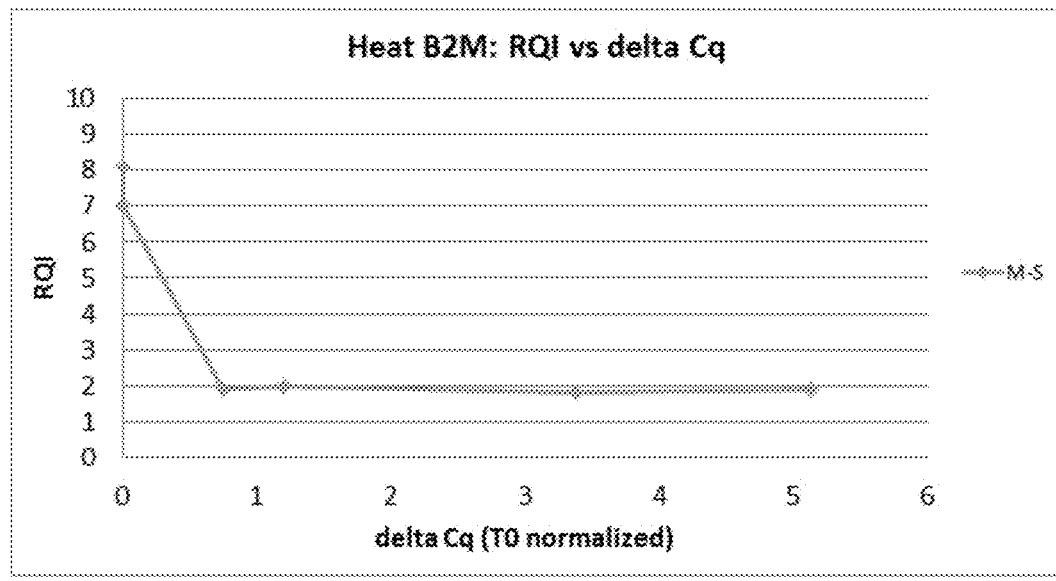

FIG. 5C shows the L:M, L:S and M:S ratios of B2M measured as function of heat inactivation. All three ratios increase with incubation time. The L:M and L:S ratios can only be followed for the first 20 minutes of degradation. There after the long B2M assay is degraded to such extent that the measured Cq values become uncertain. Still, degradation beyond 20 minutes is monitored by the M.S ratio. This demonstrates the strength of the method disclosed herein where very wide dynamic range is obtained by using three different lengths amplicons to monitor the degradation. Comparison with current state of capillary electrophoresis quantified as RQI is shown in FIG. 5D. Also with the B2M marker using the method disclosed here a much wider dynamic range is obtained than with current state of the art electropherograms.

Finally, the RNA was also analyzed using MTCO1 as marker for the here invented method to assess mRNA quality by measuring different length amplicons. The following primers were used:

```
Primers for Assay Long (L), amplicon length
295 bp:
                                       (SEQ ID NO: 27)
Forward: CCCGATATGGCGTTTCCCCGC (SEQ ID NO: 28)
Reverse: CGGATCAGACGAAGAGGGGCGT Primers for Assay Medium (M), amplicon length
176 bp:
                                       (SEQ ID NO: 29)
Forward: CCCGATATGGCGTTTCCCCGC (SEQ ID NO: 30)
Reverse: AAGATGGTTAGGTCTACGGAGGCTC Primers for Assay Short (S), amplicon length
80 bp:
                                       (SEQ ID NO: 31)
Forward: CCCGATATGGCGTTTCCCCGC (SEQ ID NO: 32)
Reverse: GCAGATGCGAGCAGGAGTAGGA
```

Figure 5E:
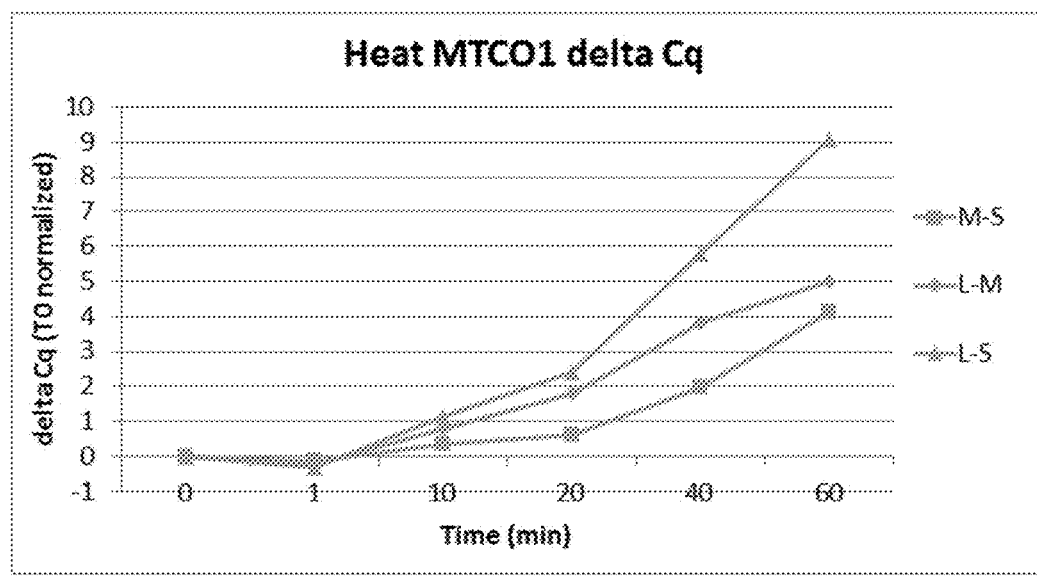

FIG. 5E shows the M:L, S:L and S:M MTCO1 ratios measured as function of heat inactivation. All three ratios increase with incubation time and the mRNA degradation is obvious.

EXAMPLE 5

Assessing RNA Degradation Induced by UV Radiation

Figure 6A:
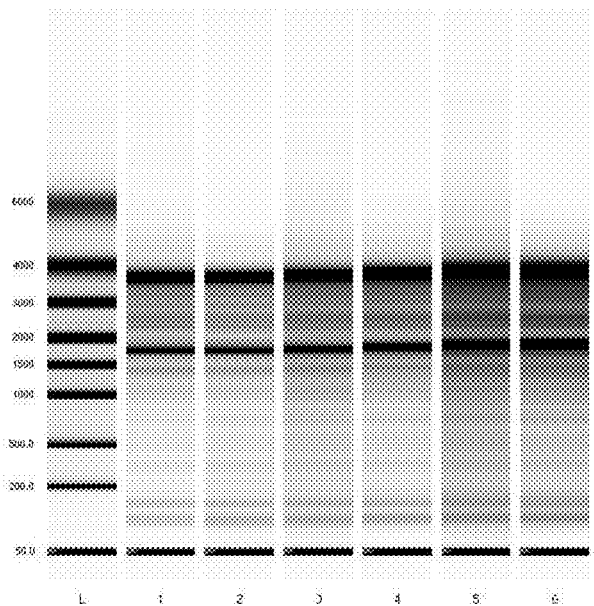
Figure 6B:
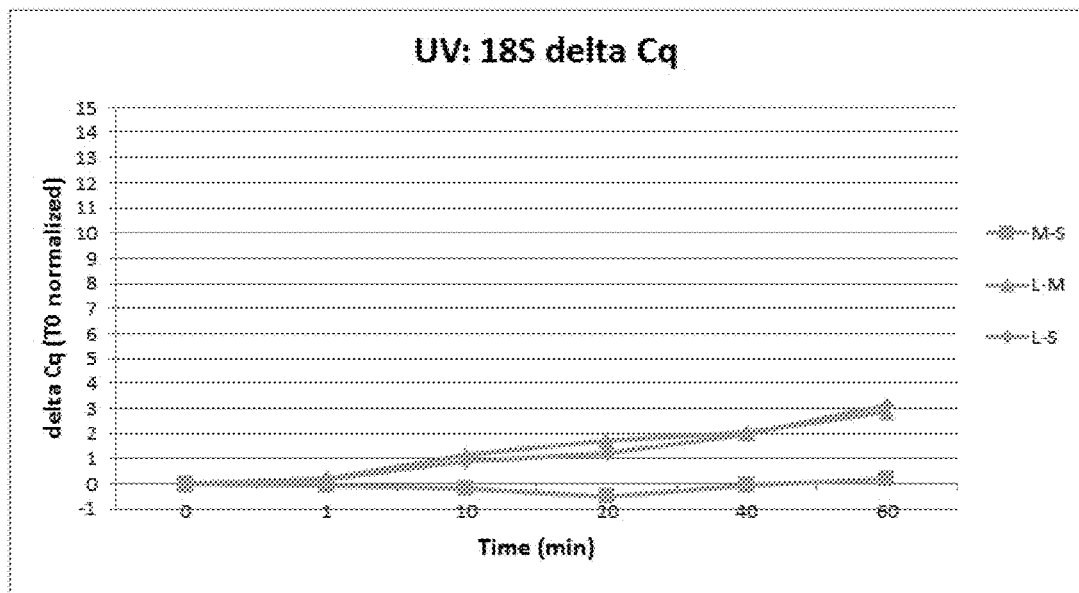
Figure 6C:
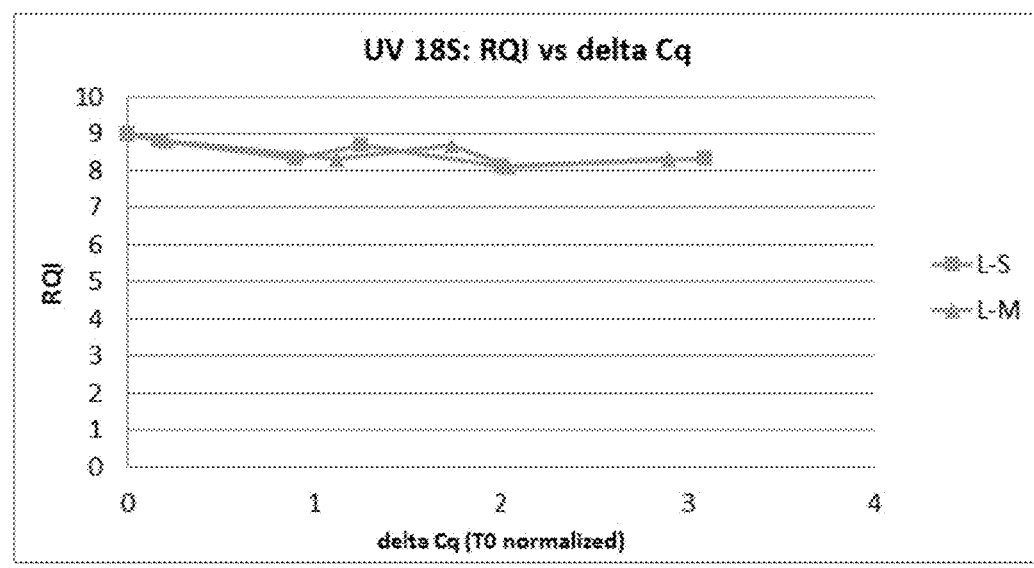
Figure 6D:
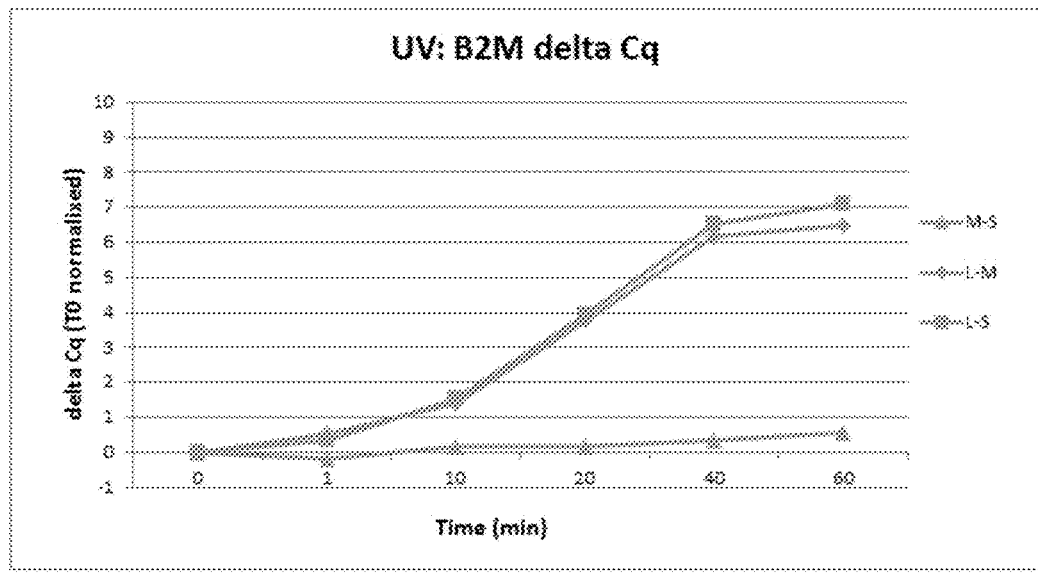
Figure 6E:
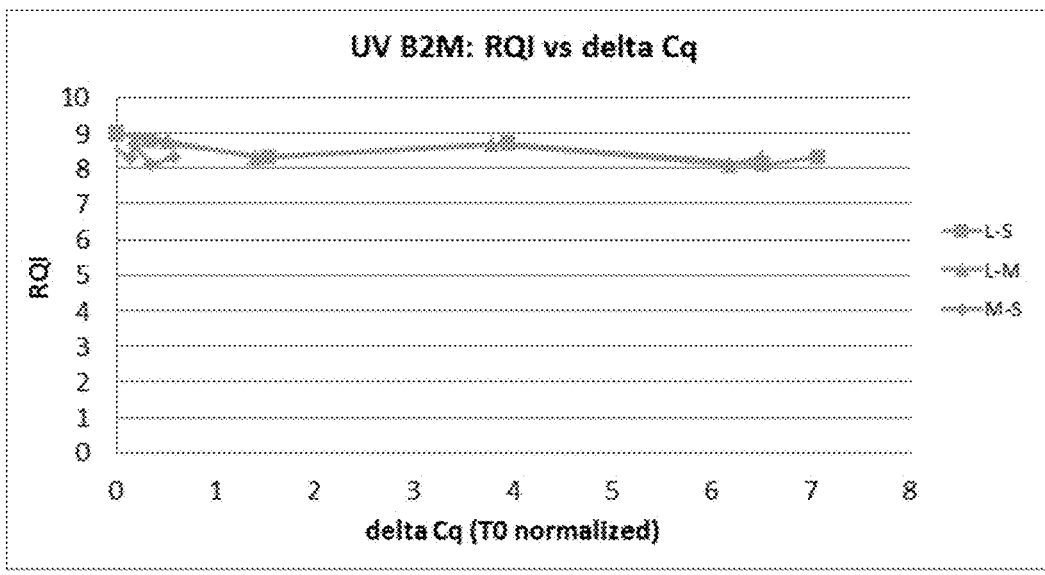
Figure 6F:
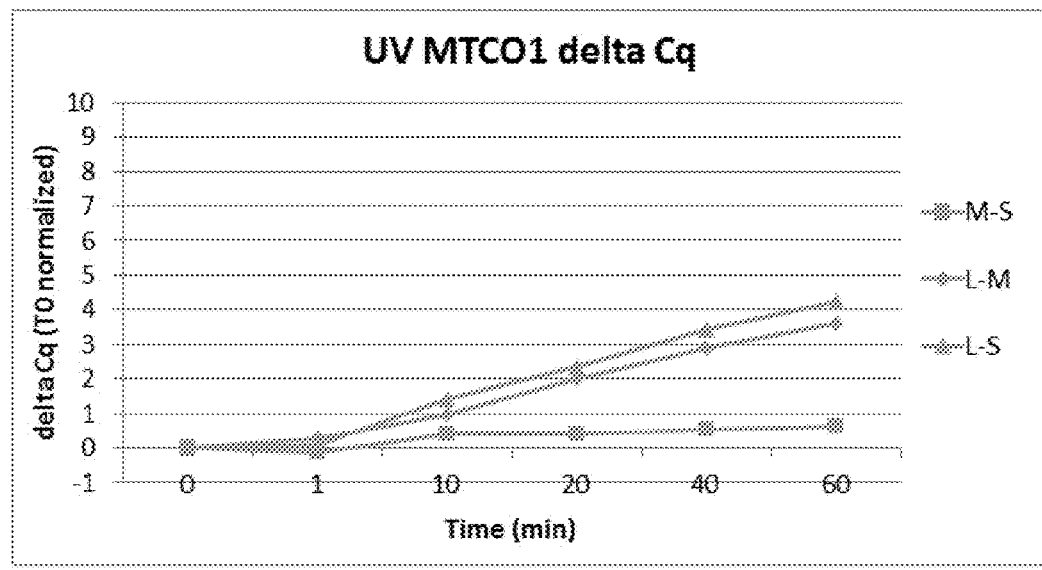

A pool of human RNA (90 ng/µl) placed in a 1.5 ml Eppendorf tube was exposed to UV light. The tube had thin plastic cover to mitigate the effect of the UV radiation. 10 µl fractions were removed after 0, 1, 10, 20, 40 and 60 minutes for analysis by capillary electrophoreses or by RT-qPCR. The RNA quality was tested according to the present description based on differential PCR yields of amplicons of varying length using the same markers (18S, B2M and MITCO1) as in Example 4. The RNA degradation was also monitored using state of the art capillary electrophoresis on the Bio-Rad Experion™ calculating RQI values from the electropherogram. The measured electropherograms as function UV irradiation are shown in FIG. 6A. Only very small changes are seen by visual inspection, which is reflected by the calculated RQI values. FIG. 6B shows changes in the M:L, S:L and S:M ratios using marker 18S. The S:M ratio stays essentially constant, reflecting very modest degradation. The M:L and S:L ratios, however, are sensitive to the degradation and increase with irradiation time. FIG. 6C compares the measured M:L and S:L ratios according to the disclosure with the state of the art capillary electrophoresis. As seen, the change in RQI values upon the imposed UV irradiation is very modest, with a decrease from 9 to about 8 over the 60 minutes, while the M:L and S:L ratios increase more than 3-fold. This comparison clearly demonstrates the superior sensitivity of the method described herein compared to current state of the art. FIG. 6D shows the same samples analyzed using marker B2M according to the present description. Also here the M:L and S:L ratios increase clearly and substantially reflecting degradation. The M:L and S:L ratios even seem to approach saturation despite the degradation being modest based on capillary electrophoresis. Here an increase is even seen for the S:M ratio. This ratio does not saturate, rather it takes off around 60 minutes suggesting this indicator could be used to monitor UV degradation for much longer. Comparison of the measured relative amplicon yields based on the present description and RQI numbers determined using current state of the art in FIG. 6E reflects again the much higher sensitivity of the here invented method. Results obtained using the method described herein with marker MTCO1 are shown in FIG. 6F. Also here the three yield ratios based on the different length amplicons increase with time of UV irradiation. Largest effect is found for the S:L ratio followed by the M:L ratio. The S:M ratio barely takes off, approaching a difference in Cq of 1 after 60 minutes, and could be used to monitoring degradation over much longer time.

EXAMPLE 6

RNA Degradation at Ambient Temperature and Different Length Amplicons

The liver samples left at ambient temperature to degrade RNA that were studied in examples 1 and 2 comparing the amounts of stable marker disclosed here and a reference marker, where also assayed by comparing different length amplicons of the same target as used in examples 4 and 5 to assess quality of heat or UV light degraded RNA. The following mouse primer sequences were used:

```
MTCO1_S:
                                           (SEQ ID NO: 33)
   Forward: CAGTTGGTGGTCTAACCGGAATTGT (SEQ ID NO: 34)
   Reverse: CGTGAAGCACGATGTCAAGGGA MTCO1_M:
                                           (SEQ ID NO: 35)
   Forward: CAGTTGGTGGTCTAACCGGAATTGT (SEQ ID NO: 36)
   Reverse: TGTGTCATCTAGGGTGAAGCCTGA MTCO1_L:
                                           (SEQ ID NO: 37)
   Forward: CAGTTGGTGGTCTAACCGGAATTGT (SEQ ID NO: 38)
   Reverse: TGTGGTGTAAGCATCTGGGTAGTCT
```

Results presented in FIG. 7 show that the three different length amplicons of MTCO1 are produced at the same relative amounts irrespectively of the length of degradation. Hence, different length amplicons, shown to be very sensitive to monitor degradation induced by heat or UV light, are not sensitive to spontaneous RNA degradation at ambient temperature. Rather, spontaneous RNA degradation at ambient temperature can be assessed comparing the expression of a stable RNA, such as MTCO1, 18S or U3, with that of a reference mRNA as demonstrated in Examples 1 and 2.

EXAMPLE 7

Assessing RNA Quality in FFPE Breast Tissue Samples

Figure 8A:
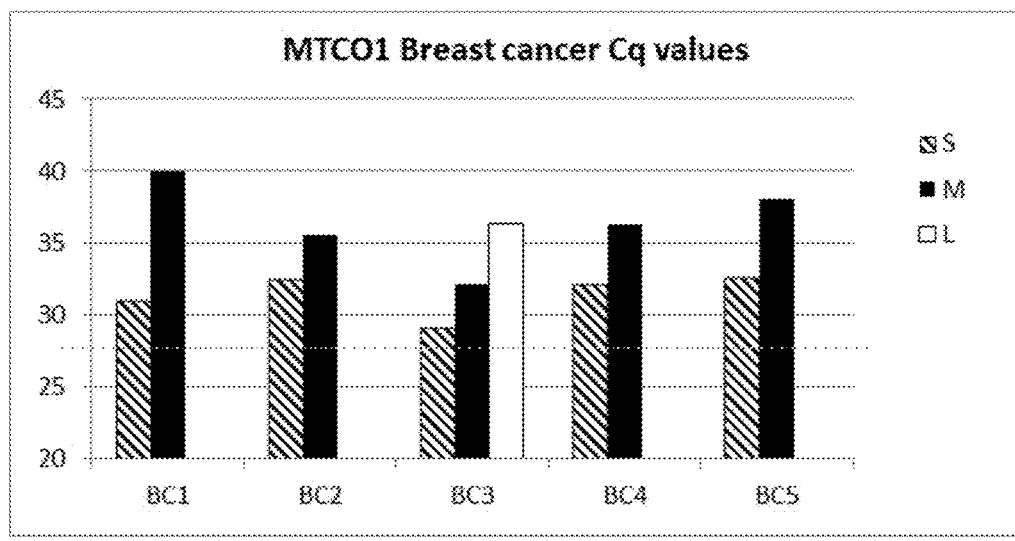
Figure 8B:
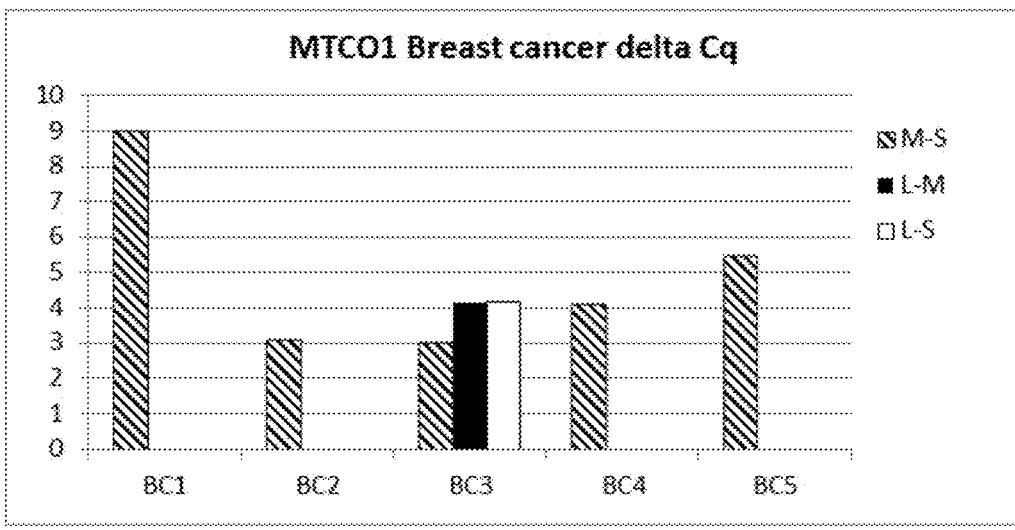
Figure 8C:
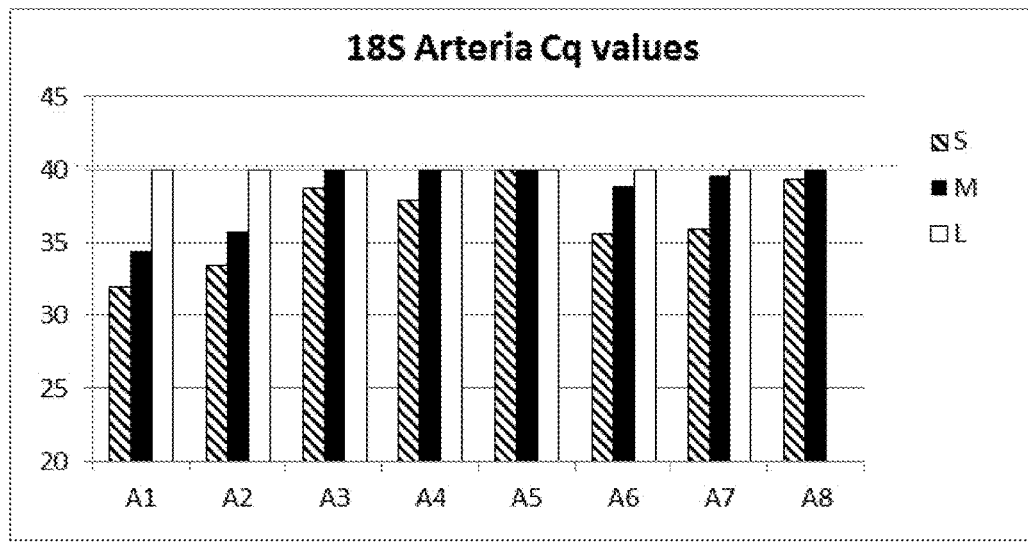

To establish the performance of the here invented method based on amplicons of different length we analyzed a set of formalin fixed paraffin embedded (FFPE) breast tissue samples. FFPE fixation is standard procedure to preserve morphology of tissue samples, but it is also known to damage RNA. The degree of RNA damage is often variable and should be assessed for analysis. Highly degraded samples are not suitable for analysis and money and resources can be saved by testing RNA quality in samples. FIG. 8A shows analysis results based on marker MTCO1 of five FFPE samples. Raw data in the form of Cq values for the three amplicons of different length are shown. For all samples it is clearly seen that highest yield (lowest Cq) is obtained for the shortest amplicon, followed by the intermediate length amplicon. Lowest yield is obtained for the longest amplicon. In fact, the longest amplicon could be measured only in sample BC3. In the other samples the yields of the longest amplicon were too low. The observed trend between the yields of the differentially long amplicons reflects the integrity of the RNA as proposed by the present description. FIG. 8B shows the data presented as differences between the measured Cq's. For these samples the difference, ΔCq (corresponding to expression ratio), based on MTCO1 is best monitored between the medium and short length amplicons.

EXAMPLE 8

Assessing RNA Quality in FFPE Arteria Samples

Figure 8D:
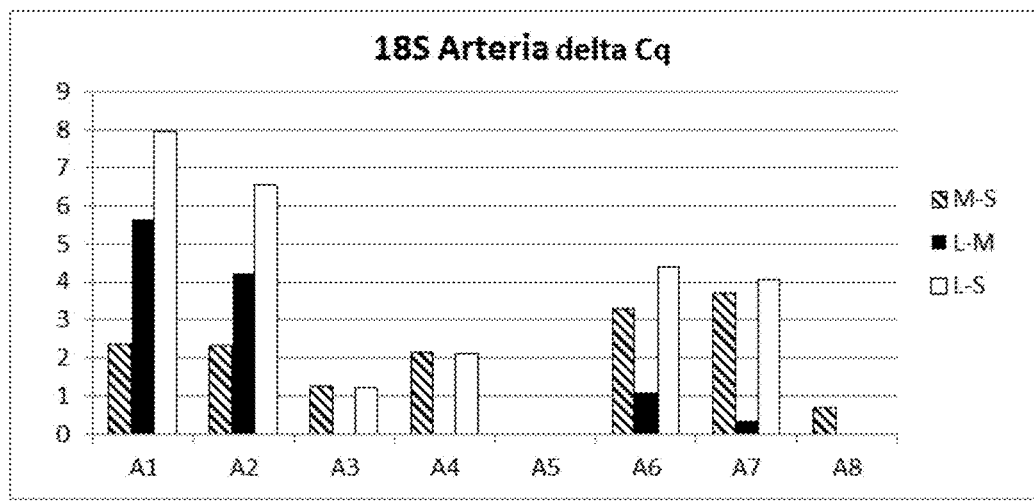

FFPE arteria samples were analyzed using 18S as marker. Three PCR's were performed yielding amplicons of three different lengths. The measured Cq values are presented in FIG. 8C. For samples A1, A2, A6 and A7 clear trend is seen with Cq increasing with amplicon length as taught herein. For samples A3 and A4 the L an M assays give no product, with Cq values saturating at 40. Since Cq could be measured for the shortest assay we still can assess reasonably the RNA quality, which here must be very poor. In sample A5 none of the three assays gave product as reflected by saturating Cq's, evidencing the RNA in this sample is totally degraded and cannot be reliably analyzed with qPCR. In sample A8 the L assay failed for unknown reason, but the RNA quality can still be assessed based on the remaining two assays. FIG. 8D presents the data as ΔCq, reflecting the relative abundance of the differentially long assays. Most reliable quantitative information for this set of data is expected from the comparison of M:S, since the L assay gave no or almost no product for most of the samples.

EXAMPLE 9

Assessing Degradation of Rat RNA Induced by Heat

A pool of rat RNA (100 ng/μl) was heated in a 1.5 ml Eppendorf tube to 95° C. 5.5 μl samples were collected at 0, 1, 10, 20, 40, 60, 120 and 240 minutes for analysis with capillary electrophoresis (Experion™ System, Bio-Rad) and subsequent RT-qPCR. FIG. 10 shows electrophoretic traces measured with the Experion™ System. The gradual degradation of ribosomal RNA with time is clearly reflected by the disappearance of two dominant slowly migrating bands and the appearance of fast migrating smear.

Two qPCR assays yielding amplicons of different length for each of the three targets, 18S RNA, B2M and MTCO1, were designed with the following primers:

```
Primers for Assay 18S RNA Long (L), amplicon
length 303 bp:
                                    (SEQ ID NO: 39)
Forward: CTAGAGCTAATACATGCCGA (SEQ ID NO: 40)
Reverse: GATGTGGTAGCCGTTTCTC Primers for Assay 18S RNA Short (S), amplicon
length 113 bp:
                                    (SEQ ID NO: 41)
Forward: CGTCTGCCCTATCAACTTTC (SEQ ID NO: 42)
Reverse: GATGTGGTAGCCGTTTCTC Primers for Assay B2M Long (L), amplicon length
337 bp:
                                    (SEQ ID NO: 43)
Forward: TGCTGTGATAAACCAAAGATGAG (SEQ ID NO: 44)
Reverse: GTCACCTGGGACCGAGAC Primers for Assay B2M Short (S), amplicon length
133 bp:
                                    (SEQ ID NO: 45)
Forward: ATGGTGTGCTCATTGCTATTC (SEQ ID NO: 46)
Reverse: GTCACCTGGGACCGAGAC Primers for Assay MTCO1 Long (L), amplicon length
334 bp:
                                    (SEQ ID NO: 47)
Forward: TAGACACCCGAGCCTACTT (SEQ ID NO: 48)
Reverse: GCTCATGTGTCATTTAGGGT Primers for Assay MTCO1 Short (S), amplicon length
108 bp:
                                    (SEQ ID NO: 49)
Forward: AGCTCACTTCCACTATGTCT (SEQ ID NO: 50)
Reverse: GCTCATGTGTCATTTAGGGT
```

The amount of PCR product produced by the L assays relative to the corresponding S assays are shown as the difference in Cq-values (deltaCq) in FIG. 9. The deltaCqs increase for all three targets with extended heating evidencing higher yields of the S assays relative to the L assays, reflecting degradation of RNA. The change is initially moderate, but increases as the degradation proceeds (time scale is shown non-linear). FIG. 9 includes comparison with the sensitivity of measurement of RNA quality by capillary electrophoresis quantified as RQI as known in the art. The initial phase of degradation reduces the RQI rapidly until it reaches a plateau at a value of about 2 after 20 minutes. After this, it is more or less constant even though continued degradation is clearly visible in the electropherograms in FIG. 10. The deltaCq for 18S RNA, however, continues to increase all the way up to 240 minutes of degradation reflecting the higher sensitivity of the novel method. The deltaCq of B2M and MTCO1 show the same trend as 18S RNA until the Cq-values for the long assays reach too high values to give reliable ratios (after 60 and 120 minutes, respectively).

EXAMPLE 10

Assessing Degradation of Rat RNA Induced by Formalin Fixation

Eight tubes, each containing 60 ng/μl rat RNA and 8.5% formalin, were incubated at room temperature for 0, 1, 10, 20, 40, 60, 120 and 240 minutes, respectively. The reactions were interrupted and the RNA purified using FFPE extraction kit (Qiagen). The RNA was analyzed with capillary electrophoresis (Experion™ System, Bio-Rad) and subsequent RT-qPCR. FIG. 12 shows electrophoretic traces measured with the Experion™ System. The RQI value in FIG. 11 shows a sharp drop between 40 and 60 minutes, which is not clearly related to changes in the electropherograms in FIG. 12. The reduction in RQI probably reflects accumulation of short fragments between 500 and 1500 bp which raises background and have substantial effect on the RQI value, while not necessarily reflecting the overall degradation. The deltaCq of the studied markers in FIG. 11 do not show any sharp change between 40 and 60 minutes. B2M shows expected smooth increase over the entire studied range and 18S RNA shows an increase only for the last two time points. The new method clearly correlates much better with overall changes in the electropherogram than the RQI does. The stable marker MTCO1 shows no significant degradation over the studied time range.

EXAMPLE 11

Assessing Enzymatically Induced Degradation of Rat RNA

Frozen rat liver was placed in a mortar filled with liquid nitrogen and grounded into powder. 20 mg powder was put in each of eight separate 1.5 ml Eppendorf tubes that were incubated at room temperature for 0, 1, 10, 20, 40, 60, 120 and 240 minutes. The RNA from each sample was extracted and analyzed with capillary electrophoresis in the Experion™ System and separately with RT-qPCR using the novel method. FIG. 14 shows the electrophoretic traces measured with the Experion™ System. The gradual degradation of ribosomal RNA with time is reflected by the disappearance of two dominant slowly migrating bands and the appearance of a fast migrating smear. This is mainly visible from 40 minutes, and is also reflected by the very slowly decreasing RQI value between 0 and 60 minutes in FIG. 13. The RQI value obviously mainly reflects the degradation of ribosomal RNA and not of the mRNA, which is of prime interest. Degradation of mRNA in the sample is clearly reflected by the increasing deltaCq of the B2M marker. The stable 18S RNA marker, that is a ribosomal RNA, is less sensitive to degradation and does better reflect more severe degradation, which occurs between 60 and 240 minutes. The stable marker MTCO1 does not show any sign of degradation even after 2 hours at room temperature.

We claim:

1. A method to assess RNA quality in a sample, the method comprising the steps of
   a) preparing cDNA from RNA,
   b) quantifying by amplification at least one amplicon of a first cDNA, wherein the first cDNA derives from mRNA,
   c) quantifying by amplification at least one amplicon of a second cDNA, wherein the second cDNA derives from a testing RNA, said testing RNA selected from a group consisting of mitochondrial cytochrome oxidase subunit 1 (MTCO1) and U3, and
   d) assessing the quality of the mRNA by comparing the amount of the at least one amplicon of the first cDNA with the amount of the at least one amplicon of the second cDNA.

2. The method of claim 1, wherein the mRNA derives from a gene with an expression that is essentially invariant of the physiological status of a cell.

3. The method of claim 1, wherein the comparison of step d) is performed using the geometric mean expression of multiple mRNAs.

4. The method of claim 1, wherein at least one of the primers used in step a) is identical to at least one of the primers used in step c).

5. A method to assess RNA quality in a sample, the method comprising the steps of
   a) preparing cDNA from RNA,
   b) quantifying by amplification at least one amplicon of a first cDNA, wherein the first cDNA derives from mRNA,
   c) quantifying by amplification at least one amplicon of a second cDNA, wherein the second cDNA derives from a testing RNA of mitochondrial cytochrome oxidase subunit 1 (MTCO1),
   d) assessing the quality of the mRNA by comparing the amount of the at least one amplicon of the first cDNA with the amount of the at least one amplicon of the second cDNA,
   e) quantifying by amplification separately from step c) at least two amplicons of the second cDNA, and
   f) assessing the quality of the testing RNA by comparing the amounts of the at least two amplicons of the second cDNA.

6. The method of claim 5, wherein the mRNA derives from a gene with an expression that is essentially invariant of the physiological status of a cell.

7. The method of claim 5, wherein at least one of the primers used in step a) is identical to at least one of the primers used in step c).

8. The method of claim 5, wherein the first of the at least two amplicons of step e) has a length of less than 100 bp and wherein the second of the at least two amplicons of step e) has a length of at least 100 bp.

9. The method of claim 5, wherein the amplification of the at least two amplicons of step e) is performed using one common primer for the at least two amplicons.

10. A method to assess RNA quality in a sample, the method comprising the steps of
    a) preparing cDNA from RNA,
    b) quantifying by amplification at least one amplicon of a first cDNA, wherein the first cDNA derives from mRNA,
    c) quantifying by amplification at least one amplicon of a second cDNA, wherein the second cDNA derives from a testing RNA of U3,
    d) assessing the quality of the mRNA by comparing the amount of the at least one amplicon of the first cDNA with the amount of the at least one amplicon of the second cDNA,
    e) quantifying by amplification separately from step c) at least two amplicons of the second cDNA, and
    f) assessing the quality of the testing RNA by comparing the amounts of the at least two amplicons of the second cDNA.

11. The method of claim 10, wherein the mRNA derives from a gene with an expression that is essentially invariant of the physiological status of a cell.

12. The method of claim 10, wherein at least one of the primers used in step a) is identical to at least one of the primers used in step c).

13. The method of claim 10, wherein the first of the at least two amplicons of step e) has a length of less than 100 bp and wherein the second of the at least two amplicons of step e) has a length of at least 100 bp.

14. The method of claim 10, wherein the amplification of the at least two amplicons of step e) is performed using one common primer for the at least two amplicons.

* * * * *